US007618963B2

(12) United States Patent
Timmers et al.

(10) Patent No.: US 7,618,963 B2
(45) Date of Patent: *Nov. 17, 2009

(54) BICYCLIC HETEROAROMATIC COMPOUNDS

(75) Inventors: Cornelis Marius Timmers, Borghem (NL); Willem Frederik Johan Karstens, Oss (NL)

(73) Assignee: N.V. Organon, Oss (NL)

( * ) Notice: Subject to any disclaimer, the term of this patent is extended or adjusted under 35 U.S.C. 154(b) by 25 days.

This patent is subject to a terminal disclaimer.

(21) Appl. No.: 11/788,886

(22) Filed: Apr. 23, 2007

(65) Prior Publication Data

US 2007/0197527 A1    Aug. 23, 2007

Related U.S. Application Data

(63) Continuation of application No. 10/381,248, filed as application No. PCT/EP01/10743 on Sep. 17, 2001, now Pat. No. 7,229,990.

(30) Foreign Application Priority Data

Sep. 22, 2000    (EP)    ................................. 00203287

(51) Int. Cl.
    *C07D 495/04*    (2006.01)
    *A61K 31/505*    (2006.01)
(52) U.S. Cl. ............ 514/234.2; 514/228.5; 514/252.16; 514/260.1; 544/61; 544/117; 544/278
(58) Field of Classification Search .................... 544/61, 544/117, 278; 514/228.5, 234.2, 252.16, 514/260.1
    See application file for complete search history.

(56) References Cited

U.S. PATENT DOCUMENTS

| 6,569,863 | B1 | 5/2003 | Gerritsma et al. | |
| 6,841,553 | B2 | 1/2005 | Gerritsma et al. | |
| 7,229,990 | B2 * | 6/2007 | Timmers et al. | ......... 514/234.2 |

FOREIGN PATENT DOCUMENTS

| WO | WO 95 34563 A | 12/1995 |
| WO | WO 00 61586 A | 10/2000 |

OTHER PUBLICATIONS

International Search Report for PCT/EP01/10743 dated Feb. 28, 2002.
Abdel-Hady et al., CAPLUS Abstract 113:40602 (1990).
Pakarainen et al., Medline Abstract.(The Journal of Clinical Investigation, vol. 115, Issue 7, pp. 1862-1868) Jul. 2005.
Huime et al., PubMed Abstract (Drugs, 64(3):297-322), 2004.
Nillius, Medscape Abstract (Clin Obstet Gynaecol. 11(3):551-72), 1984.
Stratowa, C. et al., "Use of a luciferase reporter system for characterizing G-protein-linked receptors," Current Opinion in Biotechnology, vol. 6, (1995) pp. 574-581.

Sharpe, R. M., "Intratesticular Control of Steroidogenesis," Clinical Endocrinology, vol. 33 (1990) pp. 787-807.
Dorrington, J. H. et al., "Effects of FSH on Gonadal Functions," Recent Progress in Hormone Research, vol. 35 (1979) pp. 301-342.
Insler, V., "Gonadotropin Therapy: New Trends and Insights," International Journal Fertility, vol. 33, No. 2 (1988) pp. 85-97.
Navot, D. et al., "The Use of Follicle-Stimulating Hormone for Controlled Ovarian Hyperstimulation in in Vitro Fertilization," Journal of In Vitro Fert Embryo Transfer, vol. 5, No. 1 (1988) pp. 3-13.
Morse, J. H. et al., "Heterogeneity of Proteins in Commercial Preparations of Human Chorionic Gonadotropin (hCG) Demonstrated by Western Blotting," American Journal of Reproductive Immunology and Microbiology, vol. 17 (1988) pp. 134-140.
Jia, X-C et al., "Expression of Human Luteinizing Hormone (LH) Receptor: Interaction with LH and Chorionic Gonadotropin from Human but not Equine, Rat and Ovine Species," Molecular Endocrinology, vol. 5 (1991) pp. 759-768.
Nishigaki, S. et al., "Synthetic Antibacterials. II. Synthesis of Pyrido[2,3-*d*]pyrimidine Derivatives. (I)," Chem. Pharm. Bull., vol. 18, No. 7 (1970) pp. 1385-1393.
Frye, S. V. et al., "Synthesis of 2-Aminobenzophenones via Rapid Halogen-Lithium Exchange in the Presence of a 2-Amino-*N*-methoxy-*N*-methylbenzamide," J. Org. Chem., vol. 56 (1991) pp. 3750-3752.
Bisagni, E. et al., "A convenient way to dibenzo[c,h]-1,5-naphthyridines (11-aza-benzo[c]phenanthridines," Tetrahedron, vol. 52, No. 31 (1996) pp. 10427-10440.
Blanco, M. et al., "1,6- and 1,7-Naphthyridines I. Rearrangement of Quinolinimidoacetic Acid Derivatives," J. Heterocyclic Chem., vol. 33, No. 361 (1996) pp. 361-366.
Veronese, A. C. et al., "Tin (IV) Chloride-promoted Synthesis of 4-Aminopyridines and 4- Aminoquinolines," Tetrahedron, vol. 51, No. 45 (1995) pp. 12277-12284.
Bhakta, C., "Claisen Condensation of Phthalides with Diethyl Oxalate: Formation of 3-Carbethoxy-4-hydroxyisocoumarins via Rearrangement," Indian Journal of Chemistry, vol. 25B (1986) 189-190.

(Continued)

*Primary Examiner*—Deepak Rao
(74) *Attorney, Agent, or Firm*—Susan Hess

(57) ABSTRACT

A bicyclic heteroaromatic compound according to general formula I, or a pharmaceutically acceptable salt thereof, Formula I wherein
R1 is (3-8C)cycloalkyl, (2-7C)heterocycloalkyl, (6-14C)aryl or (4-13C)heteroaryl; all optionally substituted with one or more substituents; R2 is (1-4C)alkyl, (2-4C)alkenyl, (2-4C)alkynyl, (6-14C)aryl or (4-13C)heteroaryl; R3 is (1-8C)alkyl, (3-8C)cycloalkyl, (2-7C)heterocycloalkyl, (6-14C)aryl or (4-13C)heteroaryl; Y is CH or N; Z is NH2 or OH; A is S, N(H), N(R), O or a bond and B is N(H), O or a bond; X1-X2 is C=C, C(O)—NH, NH—C(O), C(O)—O, O—C(O), C=N, N=C or S or O. The compounds of the invention can be used in fertility regulation therapies.

10 Claims, No Drawings

OTHER PUBLICATIONS

Kobayashi, K. et al., "Efficient Synthesis of 1-Amino-2-naphthalenecarboxylic Acid Derivatives via a Sequential Michael Addition/Enolate-Nitrile Coupling Route and Its Application to Facile Preparation of 9-Amino Analogues of Arylnaphthofuranone Lignans," J. Org. Chem., vol. 62, (1997) pp. 664-668.

Kobayashi, K. et al., "An Efficient General Synthesis of 1-Amino-2-naphthalenecarboxylic Acid Derivatives Based on a Tandem Conjugate Addition-Enolate Nitrile Coupling Sequence," Chemistry Letters (1996) pp. 25-26.

Boamah, P. Y. et al., "Pyrido[2,3-c]pyridazines Structurally Related to Nalidixic Acid," Arch. Pharm. (Weinheim), vol. 323 (1990) pp. 207-210.

Onda, M. et al., "Transformation of Phthalideisoquinoline Alkaloid to Benzo[c]phenanthridine Alkaloid," Chem. Pharm. Bull., vol. 20, No. 7 (1972) pp. 1484-1487.

Ishii, H. et al., "Chelirubine," Chem. Pharm. Bull., vol. 26, No. 3 (1978) pp. 864-873.

DeGraw, J. I. et al., "Synthesis and Antifolate Properties of 5,10-Ethano-5-10-dideazaaminopterin," J. Med. Chem., vol. 35 (1992) pp. 320-324.

Stadlbauer, W. et al., "Ring Closure and Rearrangement Reactions of 4-Azido-2-oxoquinoline-3-carboxylates and 4-Azidocoumarin-3-carboxylates [1]," J. Heterocyclic Chem., vol. 35 (1998) pp. 627-636.

Bessard, Y. et al., "The Preparation of Pyridinecarboxylates from Chloropyridines by the Palladium-Catalyzed Alkoxycarbonylation," Heterocycles, vol. 51, No. 11 (1999) pp. 2589-2602.

Gundersen, L-L. et al., "6-Halopurines in Palladium-Catalyzed Coupling with Organotin and Organozinc Reagents," Tetrahedron, vol. 50, No. 32 (1994) pp. 9743-9756.

Guillier, F. et al., "Synthesis of 4,5-Disubstituted Benzo[c][2,7]naphthyridines as Precursors of Pyrido[2,3,4-kl]acridones and Related Natural Products," J. Heterocyclic Chem., vol. 36 (1999) pp. 1157-1165.

Lu, Q. et al., "Trialkylalanes in Palladium-Catalyzed C-Alkylations of Azines," Acta Chemica Scandinavica, vol. 51 (1997) pp. 302-306.

Kambe, S. et al., "A One-Step Synthesis of 4-Oxo-2-thioxopyrimidine Derivatives by the Ternary Condensation of Ethyl Cyanoacetate, Aldehydes, and Thiourea," Synthesis, vol. 79 (1979) pp. 287-289.

Abd-Elfattach, A. M. et al., "Reactions with α-Substituted Cinnamonitriles: A Novel Synthesis of Arylpyrimidines," Tetrahedron, vol. 39, No. 19 (1983) pp. 3197-3199.

Hussain, S. M. et al., "A One-Step Synthesis of 2-Methylthio-6-oxopyrimidine Derivatives: Preparation of Fused Pyrimidinones," J. Heterocyclic Chem., vol. 22 (1985) pp. 169-171.

Marzinzik, A. L. et al., "Key Intermediates in Combinatorial Chemistry: Access to Various Heterocycles from α,β-Unsaturated Ketones on the Solid Phase," J. Org. Chem., vol. 63 (1998) pp. 723-727.

Masquelin, T. et al., "A Novel Solution- and Solid-Phase Approach to 2,4,5-Tri- and 2,4,5,6-Tetra-substituted Pyrimidines and Their Conversion into Condensed Heterocycles," Helvetica Chimica Acta, vol. 81 (1998) pp. 646-660.

Kohra, S. et al., "Synthesis of Pyrimidine Derivatives by the Reaction of Ketene Dithioacetals with Amides," J. Heterocyclic Chem., vol. 25 (1988) pp. 959-968.

Santilli, A. A. et al., "Thieno[2,3-d]pyrimidines. I. A New Method for the Preparation of Esters and Amides of Thieno[2,3-d]pyrimidine-6-carboxylic Acids," J. Heterocyclic Chem., vol. 8 (1971) pp. 445-453.

Clark, J. et al., "Synthesis of Thieno[2,3-d]pyrimidines from 4,6-Dichloropyrimidine-5-carbaldehydes," J. Heterocyclic Chem., vol. 30 (1993) pp. 1065-1072.

Tumkevičius, S., "A Facile Synthesis of 5H-1-Thia-3,5,6,8-tetraazaacenaphthylenes," Liebigs Ann. (1995) pp. 1703-1705.

Milart, P. et al., "Synthesis of Di- and Triamino-1,1':3',1''-terphenyls from Arylethylidene- and Arylidenemalonodinitriles, Tetrahedron, vol. 54 (1998) pp. 15643-15656.

Peseke, K. et al., "Push-pull-Butadiene; Darstellung von substituierten Dihydropyridincarbonitrilen," Z. Chem., vol. 29 (1989) pp. 442-443.

Jain, R. et al., "A One-Step Preparation of Functionalized 3- Cyano-2-Pyridones," Tetrahedron Letters, vol. 36, No. 19 (1995) pp. 3307-3310.

* cited by examiner

BICYCLIC HETEROAROMATIC COMPOUNDS

This application is a continuation of Ser. No. 10/381,248 filed Mar. 21, 2003 now U.S. Pat. No. 7,229,990 which is a 371 of PCT/EP01/10743 filed Sep. 17, 2001.

FIELD OF THE INVENTION

The invention relates to compounds having glycoprotein hormone agonistic or antagonistic activity, in particular to compounds having Luteinizing Hormone (LH) agonistic activity. The invention furthermore relates to bicyclic heteroaromatic derivatives, to pharmaceutical compositions containing the same as well as to the use of these compounds in medical therapy, particularly for use as a control of fertility.

BACKGROUND OF THE INVENTION

Gonadotropins serve important functions in a variety of bodily functions including metabolism, temperature regulation and the reproductive process. The hypophyseal gonadotropin FSH for example plays a pivotal role in the stimulation of follicle development and maturation whereas LH induces ovulation (Sharp, R. M. Clin Endocrinol. 33:787-807, 1990; Dorrington and Armstrong, Recent Prog. Horm. Res. 35:301-342, 1979). Currently, LH is applied clinically, in combination with FSH, for ovarian stimulation i.e. ovarian hyperstimulation for in vitro fertilisation (IVF) and induction of ovulation in infertile anovulatory women (Insler, V., Int. J. Fertility 33:85-97, 1988, Navot and Rosenwaks, J. Vitro Fert. Embryo Transfer 5:3-13, 1988), as well as for male hypogonadism and male infertility.

Gonadotropins act on specific gonadal cell types to initiate ovarian and testicular differentiation and steroidogenesis. The actions of these pituitary and placental hormones are mediated by specific plasma membrane receptors that are members of the large family of G-protein coupled receptors. They consist of a single polypeptide with seven transmembrane domains and are able to interact with the Gs protein, leading to the activation of adenyl cyclase.

Gonadotropins destined for therapeutic purposes can be isolated from human urine sources and are of low purity (Morse et al, Amer. J. Reproduct. Immunol. and Microbiology 17:143, 1988). Alternatively, they can be prepared as recombinant gonadotropins.

As with other therapeutic proteins, it is necessary to administer gonadotropins either subcutaneous or intra-muscular. It would be advantageous, however, to activate the receptor with a small molecule that could be administered through e.g. the oral or transdermal route.

DETAILED DESCRIPTION OF THE INVENTION

The present invention describes the preparation of such low molecular weight hormone analogs that selectively activate one of the gonadotropin receptors. This should be considered as one of the major advantages of the present invention.

Thus, the invention resides in bicyclic heteroaromatic derivatives according to general formula I, or a pharmaceutically acceptable salt thereof,

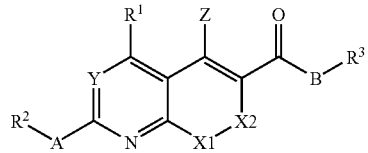

Formula I wherein $R^1$ is (3-8C)cycloalkyl, (2-7C)heterocycloalkyl, (6-14C)aryl or (4-13C)heteroaryl; preferably $R^1$ is (6-14C)aryl or (4-13C)heteroaryl;

$R^2$ is (1-4C)alkyl, (2-4C)alkenyl, (2-4C)alkynyl, or (6-14C)aryl or (4-13C)heteroaryl;

$R^3$ is (1-8C)alkyl, (3-8C)cycloalkyl, (2-7C)heterocycloalkyl, (6-14C)aryl or (4-13C)heteroaryl;

Y is CH or N;

Z is $NH_2$ or OH;

A is S, N(H), N($R^4$), O or a bond and $R^4$ can be selected from the same groups as described for $R^2$ and B is N(H), O or a bond.

The ring system in $R^1$ may optionally be substituted with one or more substituents selected from $R^5$, $NHR^5$, $N(R^4)R^5$, $OR^5$ and/or $SR^5$ in which $R^5$ is (6-14C)aryl, (4-13C)heteroaryl, (6-14C)arylcarbonyl, (2-7C)heterocycloalkyl, (3-8C)cycloalkyl, (6-14C)arylsulfonyl, (6-14C)arylaminocarbonyl, (6-14C)aryloxycarbonyl, (6-14C)arylaminosulfonyl, (6-14C)aryloxysulfonyl, (2-8C)alkenyl, (2-8C)alkynyl, (2-7C)heterocycloalkylcarbonyl, (2-8C)alkenylsulfonyl, (2-8C)alkenoxycarbonyl or (1-8C)alkyl, (1-8C)alkylcarbonyl, (1-8C)alkylsulfonyl, (1-8C)(di)alkylaminocarbonyl, (1-8C)alkoxycarbonyl, (1-8C)(di)alkylaminosulfonyl, or (1-8C)alkoxysulfonyl, the alkyl group of which may be optionally substituted with one or more substituents selected from hydroxyl, (1-8C)alkoxy, (2-7C)heterocycloalkyl(1-8C) alkoxy, (3-8C)cycloalkyl(1-8C)alkoxy, (6-14C)aryl(1-8C) alkoxy, (4-13C)heteroaryl(1-8C)alkoxy, (2-7C)heterocycloalkyl, (3-8C)cycloalkyl, (6-14C)aryl, (4-13C)heteroaryl, (1-8C)alkoxycarbonyl, (6-14C)aryloxycarbonyl, (1-8C) alkylcarbonyloxy, (6-14C)arylcarbonyloxy, (1-8C)alkylcarbonyl, (6-14C)arylcarbonyl, amine, (1-8C)alkylaminocarbonyl, (6-14C)arylaminocarbonyl, (1-8C)alkylcarbonylamino, (6-14C)arylcarbonylamino, (6-14C)(di)arylamino, (di)[(1-3C)alkoxy(1-3C)alkyl]amino and/or (1-8C)(di)alkylamino. Preferably the substituents in $R^1$ are chosen from $NHR^5$ or $OR^5$. $R^5$ in any of the substituents at $R^1$ preferably is (2-7C) heterocycloalkylcarbonyl, (6-14C)arylcarbonyl or (1-8C) alkyl, (1-8C)alkylcarbonyl, or (1-8C)(di)alkylaminocarbonyl, the alkyl group of which may be optionally substituted with (2-7C)heterocycloalkyl, (4-13C)heteroaryl, (1-8C) alkoxycarbonyl, (1-8C)alkylaminocarbonyl, (1-8C)alkylcarbonylamino, (6-14C)arylcarbonylamino, amine and/or (1-8C)(di)alkylamino. The most preferred substituents at the alkylgroup are (2-7C)heterocycloalkyl, (1-8C)(di)alkylamino, amine and (1-8C)(di)alkylaminocarbonyl.

Most preferred at R1 is phenyl optionally substituted with one of the above identified substituents, the substitution being preferably at the meta position.

In the compounds according to the invention X1-X2 is C=C, C(O)—NH, NH—C(O), C(O)—O, O—C(O), C=N or N=C. If $R^5$ is (1-8C)alkylsulfonyl, (6-14C)arylsulfonyl, (1-8C)(di)alkylaminocarbonyl, (6-14C)arylaminocarbonyl, (1-8C)atkoxycarbonyl, (6-14C)aryloxycarbonyl, (1-8C)(di) alkylaminosulfonyl, (6-14C)arylaminosulfonyl, (1-8C) alkoxysulfonyl, (2-7C)heterocycloalkylcarbonyl, (2-8C)alkenylsulfonyl, (2-8C)alkenoxycarbonyl or (6-14C) aryloxysulfonyl then X1-X2 may additionally be S or O.

Preferred compounds according to the invention are compounds according to general formula I wherein B is N(H) or a bond and/or Z is $NH_2$. Amongst these preferred compounds those wherein B is N(H) or a bond and Z is $NH_2$ are especially preferred. More preferred are the compounds which preferably in addition to the above mentioned definitions of B and Z are defined by $R^1$ being (6-14C)aryl or (4-13C)heteroaryl, optionally substituted with one or more substituents selected from $N(R^4)R^5$, $NHR^5$, $R^5$, $OR^5$ and/or $SR^5$, preferably with $NHR^5$ or $OR^5$.

Preferred for Y in all the above identified compounds is N, preferred for B is N(H) or a bond. If B is a bond, $R^3$ preferably is (2-7C)heterocycloalkyl.

Furthermore, in all the above identified compounds X1-X2 preferably is C=C, C=N or N=C, most preferably C=C. If $R^5$ is (1-8C)alkylsulfonyl, (6-14C)arylsulfonyl, (1-8C)(di) alkylaminocarbonyl, (6-14C)arylaminocarbonyl, (1-8C) alkoxycarbonyl, (6-14C)aryloxycarbonyl, (1-8C)(di)alkylaminosulfonyl, (6-14C)arylaminosulfonyl, (1-8C) alkoxysulfonyl, (2-7C)heterocycloalkylcarbonyl, (2-8C) alkenylsulfonyl, (2-8C)alkenoxycarbonyl or (6-14C) aryloxysulfonyl then preferred for X1-X2 is, in addition to the above identified groups, also S.

Most preferred are compounds selected from the group tert-butyl 5-amino-2-methylthio-4-(3-((N,N-diethylamino)-carbonyloxy)-phenyl)-thieno[2,3-d]pyrimidine-6-carboxamide, tert-butyl 5-amino-2-methylthio-4-(3-(methoxycarbonylamino)-phenyl)-thieno[2,3-d]pyrimidine-6-carboxamide, tert-butyl 5-amino-2-methylthio-4-(3-(allyloxycarbonylamino)-phenyl)-thieno[2,3-d]pyrimidine-6-carboxamide, tert-butyl 5-amino-2-methylthio-4-(3-(ethoxycarbonylamino)-phenyl)-thieno[2,3-d]pyrimidine-6-carboxamide, tert-butyl 5-amino-2-methylthio-4-(3-((morpholin-4-yl)-carbonylamino)-phenyl)-thieno[2,3-d] pyrimidine-6-carboxamide, tert-butyl 5-amino-2-methylthio-4-(3-(1,2,3,6-tetrahydropyridinocarbonylamino)-phenyl)-thieno[2,3-d] pyrimidine-6-carboxamide, tert-butyl 5-amino-2-phenyl-4-(3-((N,N-dimethylamino)-carbonylamino)-phenyl)-thieno [2,3-d]pyrimidine-6-carboxamide.

Excluded from the invention are the compounds ethyl 5-hydroxy-2-methyl-4-(piperidin-1-yl)-pyrido[2,3-d]pyrimidine-6-carboxylate, ethyl 5-hydroxy-2-methyl-4-(morpholin-4-yl)-pyrido[2,3-d]pyrimidine-6-carboxylate and ethyl 5-hydroxy-2-methyl-4-(pyrrolidin-1-yl)-pyrido[2,3-d] pyrimidine-6-carboxylate.

The disclaimer relates to the disclosures in Chem. Pharm. Bull. 18(7), 1385-1393 (1970).

The term (1-8C)alkyl as used in the definition of formula I means a branched or unbranched alkyl group having 1-8 carbon atoms, for example methyl, ethyl, propyl, isopropyl, butyl, sec-butyl, tert-butyl, hexyl and octyl. (1-6C)Alkyl groups are preferred, (1-3C)alkyl groups being the most preferred.

The term (2-8C)alkenyl means a branched or unbranched alkenyl group having 2-8 carbon atoms, such as ethenyl, 2-butenyl etc. (1-6C)Alkenyl groups are preferred, (1-3C) alkenyl groups being the most preferred.

The term (2-8C)alkynyl means a branched or unbranched alkynyl group having 2-8 carbon atoms, such as ethynyl and propynyl. Most preferred are (2-4C)alkynyl groups.

The term (6-14C)aryl means an aromatic hydrocarbon group having 6-14 carbon atoms, such as phenyl, naphthyl, tetrahydronaphthyl, indenyl, anthracyl, which may optionally be substituted with one or more substituents such as—but not limited to—hydroxy, halogen, nitro, trifluoromethyl, cyano, (1-8C)alkylcarbonylamino, (1-8C)alkylaminocarbonyl or (1-8C)(di)alkylamino, the alkyl moieties having the same meaning as previously defined. More preferred are (6-10C)aryl groups. The most preferred aromatic hydrocarbon group is phenyl.

The term (3-8C)cycloalkyl means a cycloalkyl group having 3-8 carbon atoms, being cyclopropyl, cyclobutyl, cyclopentyl, cyclohexyl, cycloheptyl or cyclo-octyl.

The term (2-7C)heterocycloalkyl means a heterocycloalkyl group having 2-7 carbon atoms, preferably 2-5 carbon atoms, and at least including one heteroatom selected from N, O or S. Preferred heteroatoms are N or O. Nitrogen-containing heterocycloalkyl groups may either be connected via a carbon or a nitrogen atom. Most preferred heterocycloalkyl groups are piperidine, morpholine and pyrrolidine.

The term (2-7C)heterocycloalkylcarbonyl means a heterocycloalkyl group having 2-7 carbon atoms as previously defined, connected to a carbonyl group.

The term (1-8C)alkoxy means an alkoxy group having 1-8 carbon atoms, the alkyl moiety having the same meaning as previously defined. (1-6C)Alkoxy groups are preferred, (1-3C)alkoxy groups being the most preferred.

The term (1-8C)alkoxycarbonyl means an alkoxycarbonyl group, the alkyl group of which contains 1-8 carbon atoms and has the same meaning as previously defined. (1-6C) Alkoxycarbonyl groups are preferred, (1-3C)alkoxycarbonyl groups being the most preferred.

The term (2-8C)alkenoxycarbonyl means an alkenoxycarbonyl group, the alkenyl group of which contains 2-8 carbon atoms and has the same meaning as previously defined. (2-6C)Alkenoxycarbonyl groups are preferred, (2-3C)alkenoxycarbonyl groups being the most preferred.

The term (1-8C)alkoxysulfonyl means an alkoxysulfonyl group, the alkyl group of which contains 1-8 carbon atoms and has the same meaning as previously defined. (1-6C) Alkoxysulfonyl groups are preferred, (1-3C)alkoxysulfonyl groups being the most preferred.

The term (1-8C)(di)alkylamino means an (di)alkylamino group having 1-8 carbon atoms, the alkyl moiety having the same meaning as previously defined. More preferred are (1-6C)(di)alkylamino groups.

The term di[(1-3C)alkoxy(1-3C)alkyl]amino means a (di) [alkoxyalkyl]amino group, both the alkyl and alkoxy moieties of which having 1-3 carbon atoms and having the same meaning as previously defined.

The term (6-14C)(di)arylamino means an (di)arylamino group having 6-14 carbon atoms, the aryl moiety having the same meaning as previously defined. More preferred are (6-10C)(di)arylamino groups. The most preferred (di)arylamino group is (di)-phenylamino.

The term (1-8C)alkylthio means an alkylthio group having 1-8 carbon atoms, the alkyl moiety having the same meaning as previously defined. Most preferred are (1-4C)alkylthio groups.

The term (6-14C)aryloxycarbonyl means an aryloxycarbonyl group, the aryl group of which contains 6-14 carbon atoms, more preferably 6-10 carbon atoms and has the same meaning as previously defined. Most preferred are phenoxycarbonyl groups.

The term (6-14C)aryloxysulfonyl means an aryloxysulfonyl group, the aryl group of which contains 6-14 carbon atoms, more preferably 6-10 carbon atoms and has the same meaning as previously defined. Most preferred are phenoxysulfonyl groups.

The term (6-14C)aryl(1-8C)alkyl means an arylalkyl group having 7-22 carbon atoms, wherein the alkyl group is a (1-8C)alkyl group and the aryl group is a (6-14C)aryl group as previously defined. More preferred are (6-10C)aryl(1-4C)alkyl groups. Phenyl(1-4C)alkyl groups, such as benzyl, are the most preferred arylalkyl groups.

The term (4-13C)heteroaryl means a substituted or unsubstituted aromatic group having 4-13 carbon atoms, preferably 4-9, at least including one heteroatom selected from N, O and/or S, like imidazolyl, thienyl, benzthienyl, quinolyl, tetrahydroquinolyl, isoquinolyl, tetrahydroisoquinolyl, indolyl, acridinolyl, furyl or pyridyl. The substituents on the heteroaryl group may be selected from the group of substituents listed for the aryl group. Preferred heteroaryl groups are thienyl, furyl, pyridyl and pyrimidyl. Nitrogen-containing heteroaryl groups may either be connected via a carbon or a nitrogen atom.

The term halogen means fluorine, chlorine, bromine or iodine.

The term (2-7C)heterocycloalkyl(1-8C)alkoxy means a heterocycloalkyl group containing 2-7 carbon atoms as defined previously, attached to a (1-8C)alkoxy group, the alkoxy moiety having the meaning as previously defined. More preferred are 2-5C)heterocycloalkyl(1-4C)alkoxy groups.

The term (3-8C)cycloalkyl(1-8C)alkoxy means a cycloalkyl group containing 3-8 carbon atoms as defined previously, attached to a (1-8C)alkoxy group, the alkoxy moiety having the meaning as previously defined. More preferred are 3-6C)cycloalkyl(1-4C)alkoxy groups.

The term (6-14C)aryl(1-8C)alkoxy means an aryl group containing 6-14 carbon atoms as defined previously, attached to a (1-8C)alkoxy group, the alkoxy moiety having the meaning as previously defined. More preferred are (6-10C)aryl(1-4C)alkoxy groups, phenyl(1-4C)alkoxy groups being the most preferred. (4-13C)Heteroaryl(1-8C)alkoxy groups are analogs of the (6-14C)aryl(1-8C)alkoxy groups, at least including one heteroatom selected from N, O and S in the heteroaryl ring. More preferred are (4-9C)heteroaryl(1-4C)alkoxy groups.

The term (1-8C)alkylcarbonyl means an alkylcarbonyl group, the alkyl group of which contains 1-8 carbon atoms and has the same meaning as previously defined. More preferred are (1-6C)alkylcarbonyl groups, (1-4C)alkylcarbonyl groups being the most preferred.

The term (6-14C)arylcarbonyl means an arylcarbonyl group, the aryl group of which contains 6-14 carbon atoms and has the same meaning as previously defined. More preferred are (6-10C)arylcarbonyl groups, phenylcarbonyl groups being the most preferred.

The term (1-8C)alkylsulfonyl means an alkylsulfonyl group, the alkyl group of which contains 1-8 carbon atoms and has the same meaning as previously defined. More preferred are (1-6C)alkylsulfonyl groups, (1-4C)alkylsulfonyl groups being the most preferred.

The term (2-8C)alkenylsulfonyl means an alkenylsulfonyl group, the alkenyl group of which contains 2-8 carbon atoms and has the same meaning as previously defined. More preferred are (2-6C)alkenylsulfonyl groups, (2-4C)alkenylsulfonyl groups being the most preferred.

The term (6-14C)arylsulfonyl means an arylsulfonyl group, the aryl group of which contains 6-14 carbon atoms and has the same meaning as previously defined. More preferred are (6-10C)arylsulfonyl groups, phenylsulfonyl groups being the most preferred.

The term (1-8C)alkylcarbonyloxy means an alkylcarbonyloxy group, the alkyl group of which contains 1-8 carbon atoms and has the same meaning as previously defined. More preferred are (1-6C)alkylcarbonyloxy groups. Most preferred are (1-4C)alkylcarbonyloxy groups.

The term (6-14C)arylcarbonyloxy means an arylcarbonyloxy group, the aryl group of which contains 6-14 carbon atoms and has the same meaning as previously defined. More preferred are (6-10C)arylcarbonyloxy groups, phenylcarbonyloxy groups being the most preferred.

The term (1-8C)(di)alkylaminocarbonyl means a (di)alkylaminocarbonyl group, the alkyl group of which contains 1-8 carbon atoms and has the same meaning as previously defined. More preferred are (1-6C)(di)alkylaminocarbonyl groups, (1-4C)(di)alkylaminocarbonyl groups being the most preferred.

The term (6-14C)(di)arylaminocarbonyl means a (di)arylaminocarbonyl group, the aryl group of which contains 6-14 carbon atoms and has the same meaning as previously defined. More preferred are (6-10C)(di)arylaminocarbonyl groups, (di)-phenylaminocarbonyl groups being the most preferred.

The term (1-8C)(di)alkylaminosulfonyl means a (di)alkylaminosulfonyl group, the alkyl group of which contains 1-8 carbon atoms and has the same meaning as previously defined. More preferred are (1-6C)(di)alkylaminosulfonyl groups, (1-4C)(di)alkylaminosulfonyl groups being the most preferred.

The term (6-14C)(di)arylaminosulfonyl means a (di)arylaminosulfonyl group, the aryl group of which contains 6-14 carbon atoms and has the same meaning as previously defined. More preferred are (6-10C)(di)arylaminosulfonyl groups, (di)-phenylaminosulfonyl groups being the most preferred.

The term (1-8C)alkylcarbonylamino means an alkylcarbonylamino group, the alkyl group of which contains 1-8 carbon atoms and has the same meaning as previously defined. More preferred are (1-6C)alkylcarbonylamino groups, (1-4C)alkylcarbonylamino groups being the most preferred.

The term (6-14C)arylcarbonylamino means an arylcarbonylamino group, the aryl group of which contains 6-14 carbon atoms and has the same meaning as previously defined. More preferred are (6-10C)arylcarbonylamino groups, phenylcarbonylamino groups being the most preferred.

The term (2-7C)heterocycloalkyloxy means a heterocycloalkyl group containing 2-7 carbon atoms as defined previously, attached to an oxygen atom. Most preferred are (2-5C) heterocycloalkyloxy groups.

The term (3-8C)cycloalkyloxy means a cycloalkyl group containing 3-8 carbon atoms as defined previously, attached to an oxygen atom.

The term (6-14C)aryloxy means an aryl group containing 6-14 carbon atoms as defined previously, attached to an oxygen atom. More preferred are (6-10C)aryloxy groups, phenoxy groups being most preferred. (4-13C)Heteroaryloxy groups are analogs of the (6-14C)aryloxy groups, at least including one heteroatom selected from N, O and S in heteroaryl ring. More preferred are (4-9C)heteroaryloxy groups.

It has been shown that compounds of the above mentioned formula I are capable of binding to the LH receptor and show agonistic LH activity.

The invention further resides in a pharmaceutical composition comprising a bicyclic heteroaromatic derivative or salts thereof having the general formula I.

Thus, the compounds according to the invention can be used in therapy. A further aspect of the invention resides in the use of a bicyclic heteroaromatic compound having the general formula I for the manufacture of a medicament for the control of fertility. Preferably the present compounds are used to activate the LH receptor.

The bicyclic heteroaromatic derivatives of this invention may possess one or more chiral carbon atoms. The compounds may therefore be obtained as chirally pure compounds or as a mixture of diastereomers and/or enantiomers. Methods for obtaining the chirally pure compounds are well known in the art, e.g. crystallization or chromatography.

For therapeutic use, salts of the compounds of formula I are those wherein the counterion is pharmaceutically acceptable. However, acid addition salts of bases according to formula I, may also find use, for example, in the preparation or purification of a pharmaceutically acceptable compound. All salts, whether pharmaceutically acceptable or not, are included within the ambit of the present invention.

Examples of acid addition salts include those derived from mineral acids such as hydrochloric acid, phosphoric acid, sulphuric acid, preferably hydrochloric acid, and organic acids like citric acid, tartaric acid, acetic acid, lactic acid, maleic acid, malonic acid, fumaric acid, glycolic acid, succinic acid, and the like.

Suitable administration routes for the compounds of formula I or pharmaceutically acceptable salts thereof, also referred to herein as the active ingredient are intramuscular injections, subcutaneous injections, intravenous injections or intraperitoneal injections, oral and intranasal administration. Preferably, the compounds may be administered orally. The exact dose and regimen of administration of the active ingredient, or a pharmaceutical composition thereof, will necessarily be dependent upon the therapeutic effect to be achieved (treatment of infertility; contraception), and may vary with the particular compound, the route of administration, and the age and condition of the individual subject to whom the medicament is to be administered.

In general parenteral administration requires lower dosages than other methods of administration which are more dependent upon adsorption. However, a dosage for humans preferably contains 0.0001-25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

In case of in vitro or ex vivo applications, like in IVF applications, the compounds of the inventions are to be used in the incubation media in a concentration of approximately 0.01-5 µg/ml.

The present invention thus also relates to pharmaceutical compositions comprising a bicyclic heteroaromatic compound according to formula in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration. The compositions may be prepared by any method well known in the art of pharmacy, for example, using methods such as those described in Gennaro et al., Remington's Pharmaceutical Sciences (18th ed., Mack Publishing company, 1990, see especially Part 8: *Pharmaceutical Preparations and Their Manufacture*).

Such methods include the step of bringing in association the active ingredient with any auxiliary agent. The auxiliary agent(s), also named accessory ingredients, include those conventional in the art (Gennaro, supra), such as, fillers, binders, diluents, disintegrants, lubricants, colorants, flavoring agents and wetting agents.

Pharmaceutical compositions suitable for oral administration may be presented as discrete dosage units such as pills, tablets or capsules, or as a powder or granules, or as a solution or suspension. The active ingredient may also be presented as a bolus or paste. The compositions can further be processed into a suppository or enema for rectal administration.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example, water prior to use.

Compositions, or formulations, suitable for administration by nasal inhalation include fine dusts or mists which may be generated by means of metered dose pressurized aerosols, nebulisers or insufflators.

The bicyclic heteroaromatic derivatives of the invention can also be administered in the form of implantable pharmaceutical devices, consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in European Patent 0,303,306 (AKZO N. V.).

Thus, the compounds according to the present invention can be used for the same clinical purposes as the native LH, with the advantage that they display altered stability properties and can be administered differently.

The compounds of the present invention wherein B=NH, represented by formula (I-a) can generally be prepared following art-known condensation of an acid of formula (II) with an amine of formula (III).

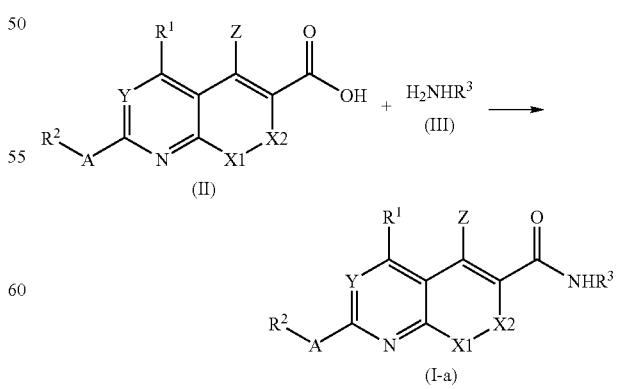

The above mentioned reaction is conducted at room temperature in a suitable solvent, e.g. an aprotic solvent such as N,N-dimethylformamide (DMF) or dichloromethane, using a coupling reagent such as O-(benzotriazol-1-yl)-N,N,N',N'-tetramethyluronium tetrafluoroborate (TBTU) or bromotripyrrolidinophosphonium hexafluorophosphate (PyBrOP) and a tertiary amine base, e.g. N,N-diisopropylethylamine (DiPEA).

Likewise, compounds of formula (I) wherein B=O, being represented by formula (I-b) can be prepared in the same way as described above for compounds of formula (I-a), starting from acids with the general structure (II) and alcohols of formula (IV).

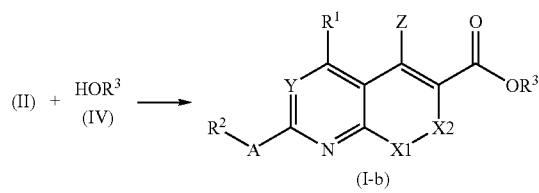

The compounds of formula (I) wherein B is a bond, represented by formula (I-c) are accessible by reaction of an appropriate organometallic reagent with derivatives of formula (V) in an aprotic solvent such as THF. Related substitution reactions can be found in literature: S. V. Frye, M. C. Johnson, N. L. Valvano, J. Org. Chem. 56: 3750, 1991. Weinreb amides of formula (V) can be synthesized from acids of formula (II) and N-methoxy-N-methyl amine using the conditions described for the preparation of amides of formula (I-a).

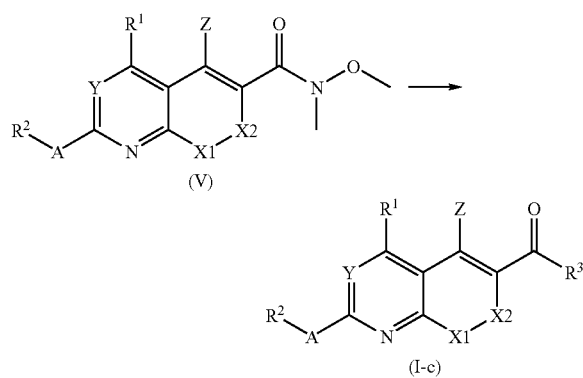

A suitable method for the preparation of intermediate acids (II) is the art-known base-mediated saponification of ethyl esters of general structure (VI). Saponification takes place in the presence of a base such as lithium hydroxide, potassium hydroxide or sodium hydroxide in aqueous dioxane at elevated temperature (40° C. to reflux), followed by acidic-work-up.

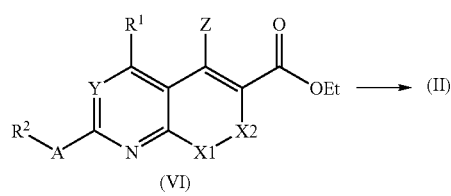

Bicyclic lactams of formula (VII) are useful starting materials for the preparation of the corresponding imines (VIII). In a typical experiment, the lactam is converted to the corresponding chloroimine using phosphoryl chloride at elevated temperature (60° C. to reflux) in an appropriate solvent such as 1,4-dioxane. Upon treatment with a reducing agent such as hydrogen in the presence of a suitable catalyst in ethanol, the desired imine of general formula (VIII) can be isolated. Related reductions have been reported in literature, see for example: E. Bisagni, C. Landras, S. Thirot and C. Huel, Tetrahedron 52: 10427, 1996.

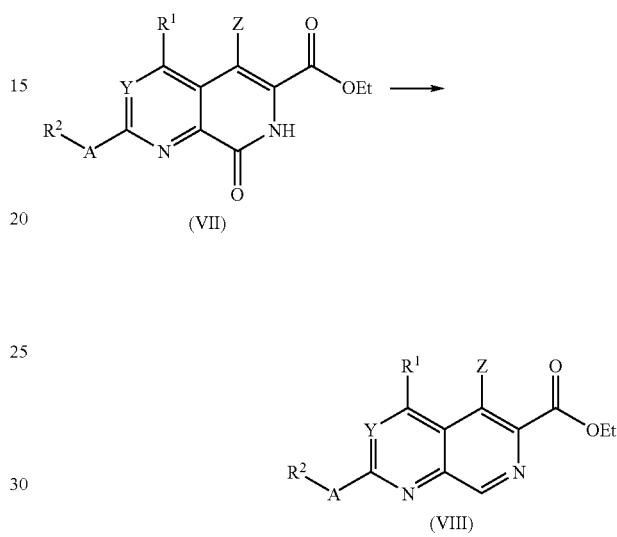

Bicyclic lactams of general structure (VII) may be prepared by condensation of acids of type (IX) with diethyl aminomalonate under the agency of a coupling agent such as TBTU/DiPEA and cyclisation of the intermediate amides in ethanol under basic conditions. Aromatisation with concomitant deethoxycarbonylation then yields bicycles of type (VII). In an alternative procedure, glycine ethyl ester can be used instead of diethyl aminomalonate. See for example: M. Blanco, M. G. Lorenzo, I. Perillo, C. B. Schapira, J. Heterocycl. Chem. 33: 361, 1996. Cyclisation of the intermediate amides may also be effected by tin(IV) chloride. The use of tin(IV) chloride to effect ring-closure on related systems has been reported: A. C. Veronese, R. Callegari, C. F. Morelli, Tetrahedron 51: 12277, 1995.

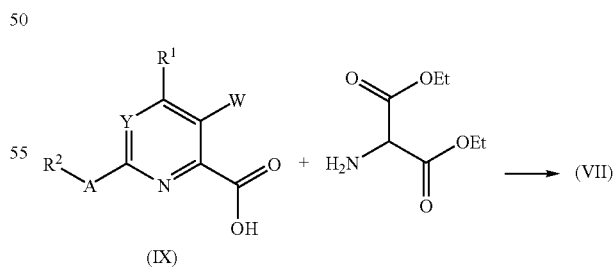

Treatment of an acid of formula (IX) with ethyl bromoacetate in an aprotic solvent under the influence of an non-nucleophilic base such as potassium carbonate or potassium tert-butoxide may give access to an aromatic lactone of general structure (X). Related structures have been described in literature: C. Bhakta, Indian J. Chem. Sect. B. 25: 189, 1986.

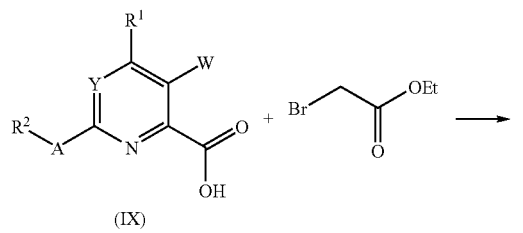

(IX)

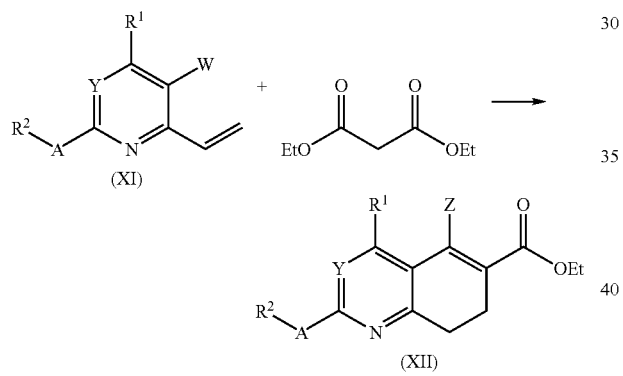

(X)

Treatment of vinyl derivatives of formula (XI) with diethyl malonate under basic conditions gives rise to conjugate addition. The intermediate adduct can be cyclised to bicycles of formula (XII) by tin(IV) chloride-mediated reaction and work-up. Alternatively, tert-butyl ethyl malonate can be used in this procedure instead of diethyl malonate.

(XI)

(XII)

Upon treatment with a suitable oxidant, such as DDQ, or with a palladium catalyst at elevated temperatures in an appropriate solvent such as xylene, aromatisation of derivatives of formula (XII) occurs to quinazolines or quinolines of general formula (XIII). See also: K. Kobayashi, T. Uneda, K. Takada, H. Tanaka, T. Kitamura, O. Morikawa, H. Konishi, J. Org. Chem. 62: 664, 1997.

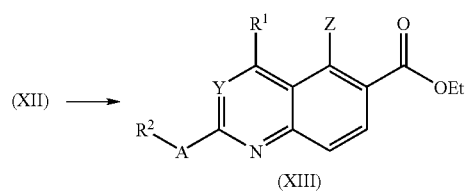

(XII) →

(XIII)

In another approach, methylpyri(mi)dines of general formula (XIV) are deprotonated at the methyl group using a strong base, such as lithium hexamethyldisilazane (LiHMDS) or lithium diisopropylamide (LDA) in a suitable aprotic solvent, such as THF at low temperatures (−78° C.). The anion is then reacted with ethyl 3-ethoxyacrylate. After conjugate addition, cyclisation to quinolines or quinazolines of general formula (XIII) occurs, as described in: K. Kobayashi, K. Takada, H. Tanaka, T. Uneda, T. Kitamura, Chem. Lett.: 25, 1996; K. Kobayashi, T. Uneda, K. Takada, H. Tanaka, T. Kitamura, O. Morikawa, H. Konishi, J. Org. Chem. 62: 664, 1997.

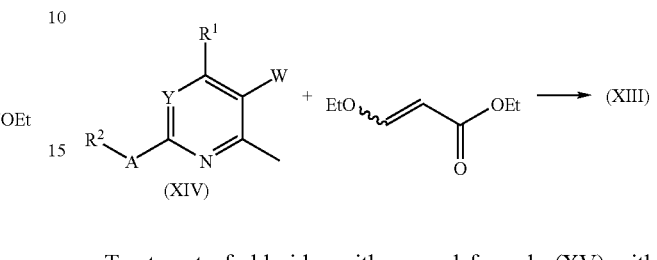

(XIV)

Treatment of chlorides with general formula (XV) with (N-alkyl)beta-alanine ethyl ester (XVI) under basic conditions gives rise to bicycles of general formula (XVII). Related transformations have been described in: P. Y. Boamah, N. Haider, G. Heinisch, Arch. Pharm. (Weinheim) 323: 207, 1990.

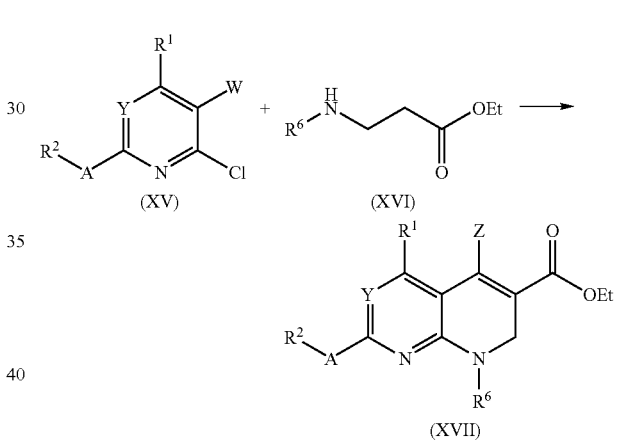

(XV)   (XVI)

(XVII)

Compounds of formula (XVII) wherein $R^6$=H can be oxidised to derivatives of formula (XVIII) using palladium on charcoal at elevated temperatures. See for example: M. Onda, K. Kawakami, Chem. Pharm. Bull. 20: 1484, 1972. Compounds of formula (XVII) wherein $R^6$=H or alkyl can be converted to imines of formula (XVIII) using DDQ, as described in: H. Ishii, Chem. Pharm. Bull. 26: 864, 1978; J. I. DeGraw, P. H. Christie, W. T. Colwell, F. M. Sirotnak, J. Med. Chem. 35: 320, 1992.

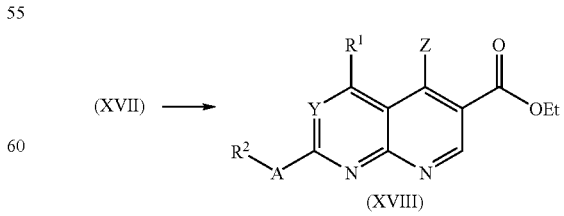

(XVII) →

(XVIII)

Alternatively, imines of formula (XVIII) can be prepared from the corresponding lactams of formula (XIX) in a similar fashion (vide supra) as their regioisomeric analogs of formula (VIII), i.e. conversion to the chloroimine using POCl$_3$ and subsequent dehalogenation using hydrogen and an appropriate catalyst.

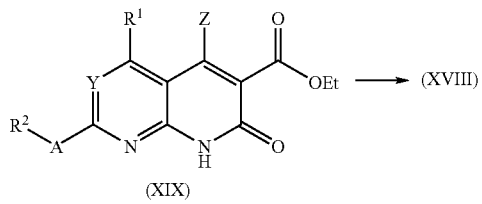

A lactam of formula (XIX) can be prepared by acylation of an aminopyri(mi)dine of formula (XX) with chloro ethyl malonate in the presence of a suitable base. Subsequent ring-closure of the intermediate acyclic malonamide under the agency of base (sodium ethoxide in ethanol) or tin(IV) chloride then affords the bicyclic lactam of type (XIX). Similar transformations have been reported in literature, see for example: A. C. Veronese, R. Callegari, C. F. Morelli, Tetrahedron 51: 12277, 1995; W. Stadlbauer, S. Prattes, W. Fiala, J. Heterocycl. Chem. 35: 627, 1998.

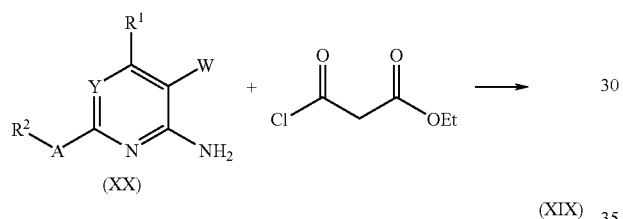

Depending on the substitution pattern of the amino pyri(mi)dines of formula (XX), lactams of formula (XIX) can be prepared by tin(IV) chloride mediated coupling of diethylmalonate, followed by cyclisation at high temperature in a suitable solvent (e.g. 240° C. in diphenyl ether).

In a similar way, lactones of type (XXII) can be prepared by O-acylation of lactams of formula (XXI) with chloro ethyl malonate and subsequent cyclisation.

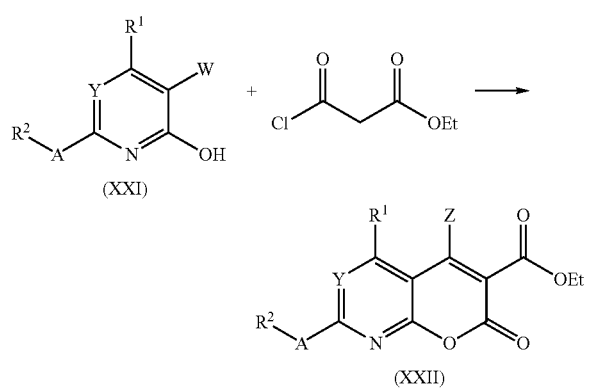

Furopyri(mi)dines of general formula (XXIII) are accessible by selective O-alkylation of lactams of type (XXI) using potassium carbonate in acetone, and subsequent ring-closure under the influence of sodium ethoxide in ethanol.

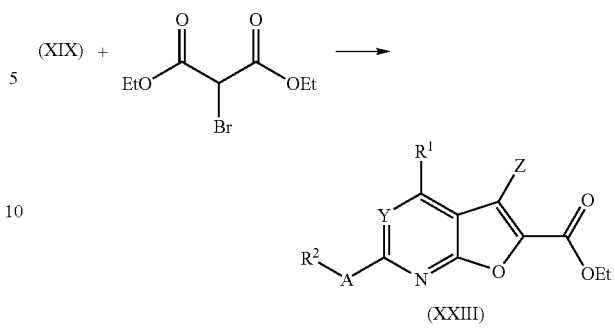

Thienopyri(mi)dines of general formula (XXIV) are accessible by treatment of chlorides (XV) with ethyl mercaptoacetate under the influence of a strong base. In a typical experiment, one equivalent of chloride (XV) is reacted with 1.5 equivalents of ethyl mercaptoacetate and 2 equivalents of potassium tert-butoxide in THF. Under these conditions, the acyclic sulfide undergoes spontaneous cyclisation to form the thienopyri(mi)dine of general formula (XXIV). If R$^1$ is (hetero)aryl, substituted with an electron withdrawing group such as nitro, the abovementioned cyclization is accomplished via a two-step procedure, involving isolation of the intermediate thioether, followed by treatment with a tertiary base such as DIPEA in toluene/EtOH at reflux temperature, to effect thiophene ring formation.

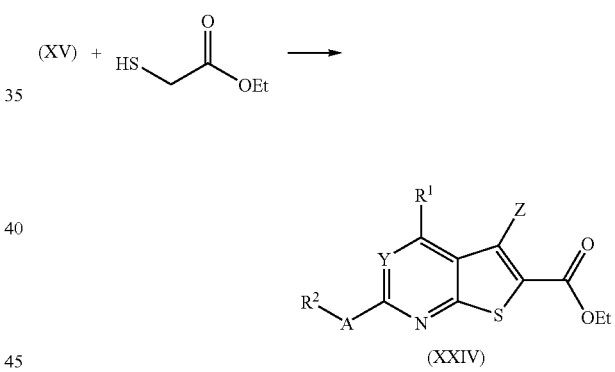

Pyri(mi)dine carboxylates of general formula (IX) are accessible by saponification of alkoxycarbonyl pyri(mi)dines of formula (XXV) using a strong base such as lithium hydroxide or potassium hydroxide in a mixture of water and an organic co-solvent such as 1,4-dioxane or methanol at elevated temperature (40° C. to reflux), followed by acidic-work-up. If W=CO$_2$alkyl, R$^7$ preferably is benzyl, to enable selective hydrogenolysis of the benzyl ester function while substituent W remains unaffected.

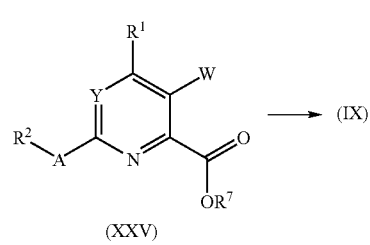

Compounds of formula (XXV) could be prepared by palladium-catalysed alkoxycarbonylation of chlorides (XV) in the presence of carbon monoxide and an appropriate alcohol (R⁷OH, XXVI). Similar transformations have appeared in literature, see for example: Y. Bessard, R. Crettaz, Heterocycles 51: 2589, 1999.

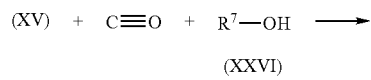

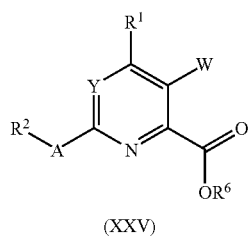

Palladium-catalysed reaction of chlorides (XV) with vinyl tributylstannane or tetravinylstannane gives access to vinyl pyri(mi)dines of general structure (XI). This type of conversions has been extensively reported in literature, see for example: L. L. Gundersen, A. K. Bakkestuen, A. J. Aasen, H. Oeveras, F. Rise, Tetrahedron 50: 9743, 1994; F. Guillier, F. Nivoliers, A. Godard, F. Marsais, G. Queguiner, J. Heterocycl. Chem. 36: 1157, 1999.

Depending on the substitution pattern of the chlorides of general formula (XV), vinyl pyri(mi)dines of general formula (XI) can also be prepared by substitution of the chloride with methylene triphenyl phosphane, followed by reaction with (para)formaldehyde.

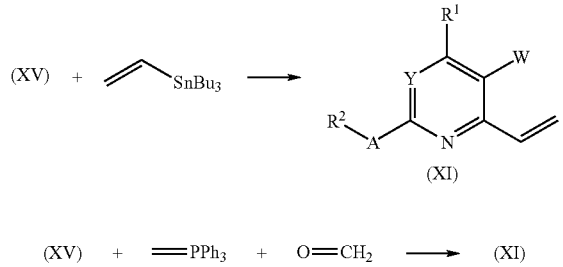

Similarly, treatment of chlorides of general formula (XV) with trimethylalane in the presence of a palladium catalyst in an aprotic solvent such as THF gives access to methylpyri(mi)dines of general formula (XIV). Related syntheses have been published in: Q. Lu, I. Mangalagiu, T. Benneche and K. Undheim, Acta Chem. Sc. 51: 302, 1997.

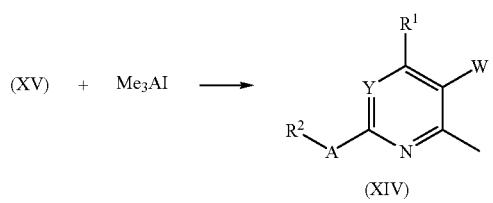

Compounds of formula (XXI) wherein Y=N, represented by formula (XXI-a) can be prepared via several literature-based approaches.

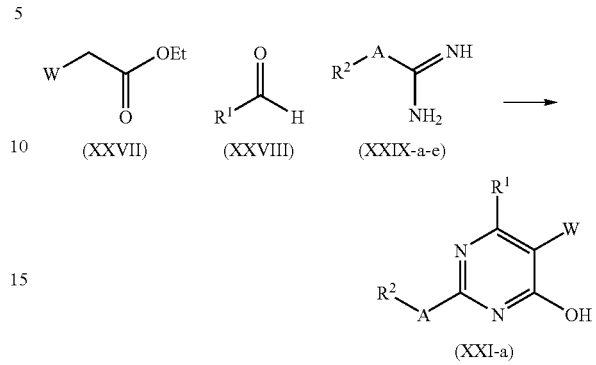

For example, derivatives of formula (XXI-a) wherein R¹=(6-14C)aryl or (4-13C)heteroaryl may be synthesized by condensation of ethyl esters (XXVII), wherein W is as previously defined, with aldehydes (XXVIII) and compounds (XXIX), which may be isothiourea (XXIX-a), isourea (XXIX-b), monosubstituted guanidines (XXIX-c), disubstituted guanidines (XXIX-d) or amidines (XXIX-e).

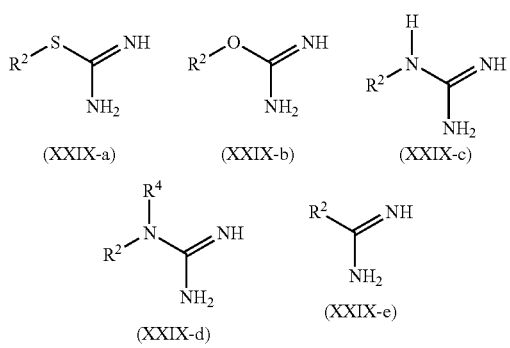

In a typical experiment, components (XXVII), (XXVIII) and (XXIXa-e) are suspended in an appropriate solvent, e.g. ethanol, methanol, N,N-dimethylformamide, N-methylpyrrolidinone, tetrahydrofuran or pyridine and a base such as potassium carbonate, sodium acetate, sodium methoxide or sodium ethoxide is added. Reaction takes place at elevated temperature (70° C. to reflux). See for example: S. Kambe, K. Saito and H. Kishi, Synthesis: 287, 1979; A. M. Abd-Elfattah, S. M. Hussain and A. M. El-Reedy, Tetrahedron 39: 3197, 1983; S. M. Hussain, A. A. El-Barbara and S. A. Mansour, J. Heterocycl. Chem. 22: 169, 1985. In the case of W=C(O) OEt, aromatization occurs on the addition of an oxidant, such as DDQ or oxygen. Related cyclizations may also be performed on a solid support such as Merrifield resin using an appropriate linker, see for example A. L. Mrzinzik and E. R. Felder, J. Org. Chem. 63: 723, 1998; T. Masquelin, D. Sprenger, R. Baer, F. Gerber and Y. Mercadal, Helv. Chim. Acta 81: 646, 1998.

Compounds of general formula (XX) wherein Y=N, represented by formula (XX-a) may be prepared via a similar condensation strategy, using malononitrile.

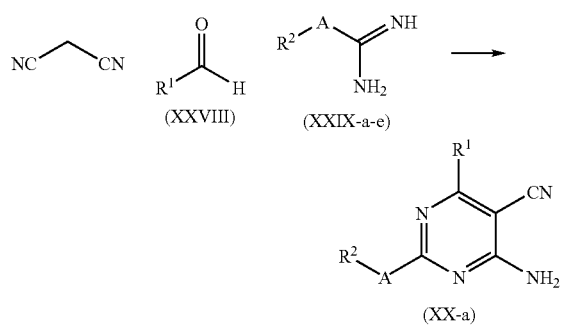

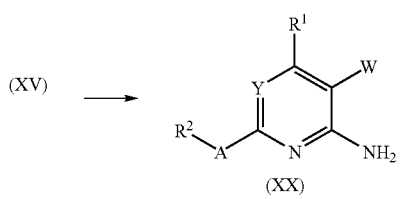

Alternatively, compounds of general formula (XX) are accessible by ammonolysis of chlorides of formula (XV), using aqueous ammonia and an appropriate organic-co solvent such as 1,4-dioxane. This transformation may also be accomplished with ammonium chloride and a tertiary amine base such as DIPEA in an aprotic solvent such as DMF.

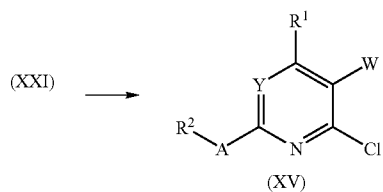

Chlorides of general formula (XV) can be synthesized by the art-known reaction of lactams (XXI) with POCl$_3$ in an appropriate solvent, such as 1,4-dioxane, at elevated temperatures (60° C. to reflux).

Derivatives of formula (XV) wherein Y=N and R$^1$ is not (6-14C)aryl or (4-13C)heteroaryl, may be prepared via monosubstitution of Cl in derivatives of formula (XXX) with various nucleophiles. Related substitution reactions can be found in literature, e.g. S. Kohra, Y. Tominaga and A. Hosomi, J. Heterocycl. Chem. 25: 959, 1988; A. A. Santilli, D. H. Kim and S. V. Wanser, J. Heterocycl. Chem. 8: 445, 1971; J. Clark, M. S. Shannet, D. Korakas and G. Varvounis, J. Heterocycl. Chem. 30: 1065, 1993; S. Tumkevicius, Liebigs Ann. Org. Bioorg. Chem. 9: 1703, 1995.

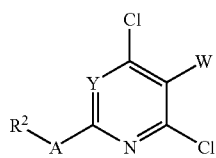

Pyridines of general formula (XXI) wherein Y=CH, A=S and W=CN, represented by formula (XXI-b) are accessible by sequential alkylation of α,β-unsaturated dinitriles of general structure (XXXI) with carbon disulfide and alkyl iodide R$^2$—I to give compounds of general formula (XXXII), as described by P. Milart, Tetrahedron 54: 15643-15656, 1998. Cyclization of compounds of formula (XXXII) under acidic conditions as described by K. Peseke, Z. Chem. 29: 442-443 (1989) yields pyridines of general formula (XXI-b).

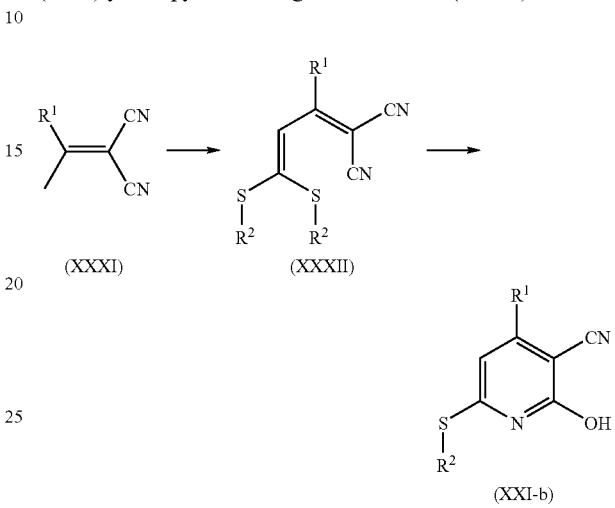

Compounds of general formula (XXI) wherein A is a bond, Y=CH and W is as previously defined, represented by formula (XXI-c), can be prepared by reaction of α, β-unsaturated ketones of general formula (XXXIII) with amides of general formula (XXXIV) wherein W is as previously defined, using a strong base such as potassium tert-butoxide in the presence of oxygen in a suitable solvent, such as dimethylsulfoxide. Related cyclisations have been described in: R. Jain, F. Roschangar, M. A. Ciufolini, Tetrahedron Lett. 36: 3307, 1995.

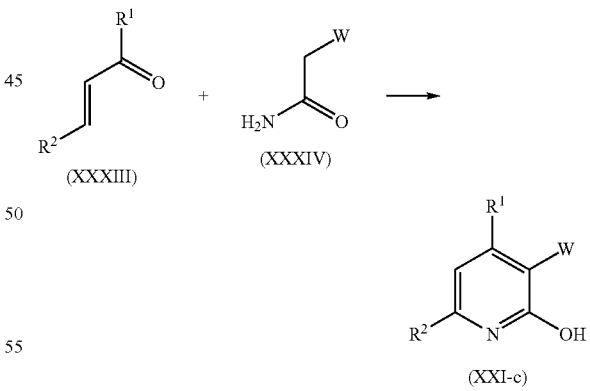

Methods to determine receptor binding as well as in vitro and in vivo assays to determine biological activity of gonadotropins are well known. In general, expressed receptor is contacted with the compound to be tested and binding or stimulation or inhibition of a functional response is measured.

To measure a functional response isolated DNA encoding the LH receptor gene, preferably the human receptor, is expressed in suitable host cells. Such a cell might be the Chinese Hamster Ovary cell, but other cells are also suitable.

Preferably the cells are of mammalian origin (Jia et al, Mol. Endocrin., 5:759-776, 1991).

Methods to construct recombinant LH expressing cell lines are well known in the art (Sambrook et al., Molecular Cloning: a Laboratory Manual, Cold Spring Harbor Laboratory Press, Cold Spring Harbor, latest edition). Expression of receptor is attained by expression of the DNA encoding the desired protein. Techniques for site directed mutagenesis, ligation of additional sequences, PCR, and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then are then contacted with the test compound to observe binding, or stimulation or inhibition of a functional response.

Alternatively isolated cell membranes containing the expressed receptor may be used to measure binding of compound.

For measurement of binding radioactively or fluorescently labeled compounds may be used. As reference compound human recombinant LH can be used. In the alternative also competition binding assays can be performed.

Another assay involves screening for LH receptor agonist compounds by determining stimulation of receptor mediated cAMP accumulation. Thus, such a method involves expression of the receptor on the cell surface of a host cell and exposing the cell to the test compound. The amount of cAMP is then measured. The level of cAMP will be reduced or increased, depending on the inhibitory or stimulating effect of the test compound upon binding to the receptor.

In addition to direct measurement of e.g. cAMP levels in the exposed cell, cells lines can be used which in addition to transfection with receptor encoding DNA are also transfected with a second DNA encoding a reporter gene the expression of which responds to the level of cAMP. Such reporter genes might be cAMP inducible or might be constructed in such a way that they are connected to novel cAMP responsive elements. In general, reporter gene expression might be controlled by any response element reacting to changing levels of cAMP. Suitable reporter genes are e.g. LacZ, alkaline phosphatase, firefly luciferase and green fluorescence protein. The principles of such transactivation assays are well known in the art and are described e.g. in Stratowa, Ch, Himmler, A and Czernilofsky, A. P. (1995) Curr. Opin. Biotechnol. 6:574. For selecting active compounds testing at $10^{-5}$ M must result in an activity of more than 20% of the maximal activity when LH is used as a reference. Another criterion might be the $EC_{50}$ value which must be $<10^{-5}$ M, preferably $<10^{-7}$ M.

The skilled artisan will recognize that desirable $EC_{50}$ values are dependent on the compound tested. For example, a compound with an $EC_{50}$ which is less than $10^{-5}$ M is generally considered a candidate for drug selection. Preferably this value is lower than $10^{-7}$ M, more preferably $10^{-8}$ M. However, a compound which has a higher $EC_{50}$, but is selective for the particular receptor, may be even a better candidate.

Screening for LH receptor agonistic compounds can also be performed by using a mouse Leydig cell bioassay (Van Damme, M., Robersen, D. and Diczfalusy, E. (1974). Acta Endocrinol. 77: 655-671 Mannaerts, B., Kloosterboer, H. and Schuurs, A. (1987). Neuroendocrinology of reproduction. R. Rolland et al. Eds., Elsevier Science Publishers B. V., 49-58). In this assay, stimulation of LH receptor mediated testosterone production can be measured in Leydig cells isolated from male mice.

To measure in vivo activity of LH receptor agonistic compounds ovulation induction in immature mice can be studied. In this assay immature female mice can be primed with urinary FSH and approximately 48 hours later treated with a LH agonistic compound. The animals are killed after LH agonist treatment and the number of ova in the oviduct can be microscopically assessed.

The compounds of the present invention can be applied clinically in those regimens where now LH or hCG is used. These include LH substitution among subjects with hypogonadal hypogonadism either male or female, midcycle administration to induce ovulation (ovulation induction (OI) or controlled hyperstimulation (COH) or stimulation of the corpus luteum.

The following examples are illustrative for the invention and should in no way be interpreted as limiting the scope of the invention.

EXAMPLES

Example 1 tert-Butyl 5-amino-2-methylthio-4-(3-(methoxycarbonyloxy)-phenyl)-thieno[2,3-d]pyrimidine-6-carboxamide (a). 5-Cyano-4-(3-methoxyphenyl)-2-methylthio-6-hydroxy-pyrimidine A mixture of S-methylisothiourea sulfate (139 mg), 3-methoxybenzaldehyde (243 µl), ethyl cyanoacetate (112 µl) and potassium carbonate (145 mg) in abs. ethanol (2 ml) was stirred at 60° C. for 5 h. The reaction mixture was cooled to 0° C. in an ice bath, filtered and the residue was heated in water ($H_2O$) until a clear solution was obtained. The solution was acidified with 2N aq. HCl to pH 2 and cooled to 0° C. in an ice bath. The resulting crystals were collected by filtration and dried in vacuo.

Yield: 186 mg

MS-ESI: $[M+H]^+=274.2$

TLC: $R_f=0.50$, silica gel, dichloromethane ($CH_2Cl_2$)/methanol ($CH_3OH$)=9/1 (v/v)

(b). 6-Chloro-5-cyano-4-(3-methoxyphenyl)-2-methylthio-pyrimidine

Phosphorus oxychloride (0.75 ml) was added to a stirred solution of 5-cyano-4-(3-methoxyphenyl)-2-methylthio-6-hydroxy-pyrimidine (example 1a, 305 mg) in dry 1,4-dioxane (1 ml). A drop of N,N-dimethylaniline was added. After 3 h at 80° C., the mixture was cooled to 0° C. in an ice bath and crushed ice was slowly added. After cessation of the exothermic reaction, $H_2O$ (3 ml) was added. The solids were collected by filtration and dried in vacuo.

Yield: 244 mg

MS-ESI: $[M+H]^+=292.2$

TLC: $R_f=0.86$, silica gel, $CH_2Cl_2$

(c). Ethyl 5-amino-4-(3-methoxyphenyl)-2-methylthio-thieno[2,3-d]pyrimidine-6-carboxylate Potassium tert-butoxide (150 mg) was added to a stirred solution of ethyl 2-mercaptoacetate (92 µl) and 6-chloro-5-cyano-4-(3-methoxyphenyl)-2-methylthio-pyrimidine (example 1b, 244 mg) in dry tetrahydrofuran (THF) (4 ml). After 1 h, the mixture was cooled to 0° C. in an ice bath, diluted with H$_2$O (10 ml). The solids were collected by filtration and dried in vacuo.

Yield: 260 mg
MS-ESI: [M+H]$^+$=376.2
TLC: R$_f$=0.44, silica gel, CH$_2$Cl$_2$

(d). 5-Amino-4-(3-methoxyphenyl)-2-methylthio-thieno[2,3-d]pyrimidine-6-carboxylic acid Ethyl 5-amino-4-(3-methoxyphenyl)-2-methylthio-thieno[2,3-d]pyrimidine-6-carboxylate (example 1c, 9.27 g) was dissolved in a mixture of 1,4-dioxane (270 ml) and H$_2$O (30 ml). Lithium hydroxide (10 g) was added and the mixture was stirred at 80° C. for 48 h. 1,4-Dioxane was removed from the mixture by evaporation and the residue was taken up in H$_2$O. The remaining solution was acidified to pH 2 by adding aq. 3N aq. HCl. The resulting precipitate was filtered off and washed with H$_2$O. Traces of water in the precipitate were removed by coevaporation with 1,4-dioxane and then with diethylether and drying in vacuo at 50° C. overnight.

Yield: 8.45 g
MS-ESI: [M+H]$^+$=348.0
TLC: R$_f$=0.2, silica gel, CH$_2$Cl$_2$/CH$_3$OH=9/1 (v/v)

(e). tert-Butyl 5-amino-2-methylthio-4-(3-methoxyphenyl)-thieno[2,3-d]pyrimidine-6-carboxamide 5-Amino-4-(3-methoxyphenyl)-2-methylthio-thieno[2,3-d]pyrimidine-6-carboxylic acid (example 1d, 7.0 g) was dissolved in dry CH$_2$Cl$_2$ (100 ml). Benzotriazol-1-yl-N,N,N',N'-tetramethyluroniumtetrafluoroborate (TBTU) (8.0 g), N,N-diisopropylethylamine (DIPEA) (6.6 ml) and tert-butylamine (4.0 ml) were added and the mixture was stirred at room temperature for 5 h. The reaction mixture was washed with 5% aq. NaHCO$_3$ (2*100 ml) and 1M aq. HCl (2*100 ml). The organic layer was dried (MgSO$_4$) and concentrated in vacuo. The title compound was purified by chromatography on silica gel with heptane (hept)/ethyl acetate (EtOAc)=1/0 to 3/2 (v/v) as eluent.

Yield: 6.5 g
MS-ESI: [M+H]$^+$=403.0
HPCL: R$_t$=33.56 min, column 3 µm Luna C-18(2) 100*2.0 mm, flow 0.25 ml/min, oven temperature 40° C., detection 210 nm+254 nm, eluent H$_2$O/acetonitrile(CH$_3$CN)/CH$_3$OH=70/28.5/1.5 to 0/95/5 (v/v) in 50 min

(f). tert-Butyl 5-amino-2-methylthio-4-(3-hydroxyphenyl)-thieno[2,3-d]pyrimidine-6-carboxamide tert-Butyl 5-amino-2-methylthio-4-(3-methoxyphenyl)-thieno[2,3-d]pyrimidine-6-carboxamide (example 1e, 1.8 g) was dissolved in dry CH$_2$Cl$_2$ (30 ml) and the resulting solution was cooled down to 0° C. A solution of boron tribromide (1.28 ml) in dry CH$_2$Cl$_2$ (30 ml) was added dropwise and the mixture was stirred overnight at room temperature. Sat. aq. NaHCO$_3$ was added dropwise to the reaction mixture until cessation of the exothermic reaction. Thereafter, CH$_2$Cl$_2$ was removed from the mixture by evaporation and a large amount of EtOAc was added. The organic layer was washed with sat. aq. NaHCO$_3$, dried (MgSO$_4$) and concentrated in vacuo.

Yield: 1.3 g
MS-ESI: [M+H]$^+$=389.2
HPCL: R$_t$=17.44 min, column Luna C-18 (see example 1e), eluent H$_2$O/CH$_3$CN/CH$_3$OH=90/9.5/0.5 to 0/95/5 (v/v) in 50 min

(g). tert-Butyl 5-amino-2-methylthio-4-(3-(methoxycarbonyloxy)-phenyl)-thieno[2,3-d]pyrimidine-6-carboxamide tert-Butyl 5-amino-2-methylthio-4-(3-hydroxyphenyl)-thieno[2,3-d]pyrimidine-6-carboxamide (example 1f, 100 mg) was dissolved in dry CH$_2$Cl$_2$ (5 ml. DIPEA (500 µl) and methyl chloroformate (199 µl) were added and the reaction mixture was stirred at room temperature overnight. The reaction mixture was washed with H$_2$O. The organic layer was dried (MgSO$_4$) and concentrated under reduced pressure. The title compound was purified by HPLC using a Luna C-18 column with the following gradient: CH$_3$CN/H$_2$O=10/90 to 90/10 (v/v) in 30 min. The title compound was then lyophilized from a mixture of 1,4-dioxane and H$_2$O.

Yield: 93 mg
MS-ESI: [M+H]$^+$=447.4
HPCL: R$_t$=17.56 min, column Luna C-18 (see example 1e), eluent H$_2$O/CH$_3$CN=40/60 to 0/100 (v/v) in 25 min

Example 2 tert-Butyl 5-amino-2-methylthio-4-(3-(allyloxycarbonyloxy)-phenyl)-thieno[2,3-d]pyrimidine-6-carboxamide The reaction of tert-butyl 5-amino-2-methylthio-4-(3-hydroxyphenyl)-thieno[2,3-d]pyrimidine-6-carboxamide (example 1f, 100 mg) with allyl chloroformate (274 µl) was performed according to the methods described in example 1g. The title compound was purified by HPLC using a Luna C-18 column with the following gradient: CH$_3$CN/H$_2$O=10/90 to 90/10 (v/v) in 30 min. The title compound was then lyophilized from a mixture of 1,4-dioxane and H$_2$O.

Yield: 102 mg
MS-ESI: [M+H]$^+$=473.4
HPCL: R$_t$=19.82 min, column Luna C-18 (see example 1e), eluent H$_2$O/CH$_3$CN=40/60 to 0/100 (v/v) in 25 min

Example 3 tert-Butyl 5-amino-2-methylthio-4-(3-(benzyloxycarbonyloxy)-phenyl)-thieno[2,3-d]pyrimidine-6-carboxamide The reaction of tert-butyl 5-amino-2-methylthio-4-(3-hydroxyphenyl)-thieno[2,3-d]pyrimidine-6-carboxamide (example 1f, 100 mg) with benzyl chloroformate (368 µl) was performed according to the methods described in example 1g. The title compound was purified by HPLC using a Luna C-18 column with the following gradient: CH$_3$CN/H$_2$O=10/90 to 90/10 (v/v) in 30 min. The title compound was then lyophilized from a mixture of 1,4-dioxane and H$_2$O.

Yield: 112 mg
MS-ESI: [M+H]$^+$=523.2

HPCL: $R_t$=22.22 min, column Luna C-18 (see example 1e), eluent $H_2O/CH_3CN$=40/60 to 0/100 (v/v) in 25 min

Example 4 tert-Butyl 5-amino-2-methylthio-4-(3-(p-nitro-benzyloxycarbonyloxy)-phenyl)-thieno[2,3-d]pyrimidine-6-carboxamide The reaction of tert-butyl 5-amino-2-methylthio-4-(3-hydroxyphenyl)-thieno[2,3d]pyrimidine-6-carboxamide (example 1f, 100 mg) with p-nitrobenzyl chloroformate (554 mg) was performed according to the methods described in example 1g. The title compound was purified by HPLC using a Luna C-18 column with the following gradient: $CH_3CN/H_2O$=10/90 to 90/10 (v/v) in 30 min. The title compound was then lyophilized from a mixture of 1,4-dioxane and $H_2O$.

Yield: 47 mg
MS-ESI: $[M+H]^+$=568.4
HPCL: $R_t$=21.45 min, column Luna C-18 (see example 1e), eluent $H_2O/CH_3CN$=40/60 to 0/100 (v/v) in 25 min

Example 5 tert-Butyl 5-amino-2-methylthio-4-(3-(phenoxycarbonyloxy)-phenyl)-thieno[2,3-d]pyrimidine-6-carboxamide The reaction of tert-butyl 5-amino-2-methylthio-4-(3-hydroxyphenyl)-thieno[2,3-d]pyrimidine-6-carboxamide (example 1f, 100 mg) with phenyl chloroformate (324 µl) was performed according to the methods described in example 1g. The title compound was purified by HPLC using a Luna C-18 column with the following gradient: $CH_3CN/H_2O$=10/90 to 90/10 (v/v) in 30 min. The title compound was then lyophilized from a mixture of 1,4-dioxane and $H_2O$.

Yield: 89 mg
MS-ESI: $[M+H]^+$=509.4
HPCL: $R_t$=21.12 min, column Luna C-18 (see example 1e), eluent $H_2O/CH_3CN$=40/60 to 0/100 (v/v) in 25 min

Example 6 tert-Butyl 5-amino-2-methylthio-4-(3-(p-nitro-phenoxycarbonyloxy)-phenyl)-thieno[2,3-d]pyrimidine-6-carboxamide The reaction of tert-butyl 5-amino-2-methylthio-4-(3-hydroxyphenyl)-thieno[2,3-d]pyrimidine-6-carboxamide (example 1f, 400 mg) with p-nitro-phenyl chloroformate (207 mg) was performed according to the methods described in example 1 g. Evaporation of the solvent under reduced pressure yielded the crude title compound.

Yield: 569 mg
MS-ESI: $[M+H]^+$=554.6
TLC: $R_f$=0.5, silica gel, hep/EtOAc=3/2 (v/v)

Example 7 tert-Butyl 5-amino-2-methylthio-4-(3-((N,N-diethylamino)-carbonyloxy)-phenyl)-thieno[2,3-d]pyrimidine-6-carboxamide tert-Butyl 5-amino-2-methylthio-4-(3-hydroxyphenyl)-thieno[2,3-d]pyrimidine-6-carboxamide (example 1f, 100 mg) was dissolved in dry $CH_2Cl_2$ (5 ml) and a few drops of N,N-dimethylformamide (DMF) were added. Diethylcarbamoyl chloride (68 mg) and DIPEA (217 µl) were added and the reaction mixture was stirred at room temperature overnight. The reaction mixture was washed with $H_2O$. The organic layer was dried ($MgSO_4$) and concentrated under reduced pressure. The title compound was purified by HPLC using a Luna C-18 column with the following gradient: $CH_3CN/H_2O$=10/90 to 90/10 (v/v) in 30 min. The title compound was then lyophilized from a mixture of 1,4-dioxane and $H_2O$.

Yield: 75 mg
MS-ESI: $[M+H]^+$=488.4
TLC: $R_f$=0.6, silica gel, hept/EtOAc=1/1 (v/v)

Example 8 tert-Butyl 5-amino-2-methylthio-4-(3-(1,2,3,6-tetrahydropyridinocarbonyloxy)-phenyl)-thieno[2,3-d]pyrimidine-6-carboxamide tert-Butyl 5-amino-2-methylthio-4-(3-(p-nitro-phenoxycarbonyloxy)-phenyl)-thieno[2,3-d]pyrimidine-6-carboxamide (example 6, 142 mg) was dissolved in $CH_2Cl_2$. 1,2,3,6-Tetrahydropyridine (117 µl) and DIPEA (224 µl) were added and the mixture was stirred at room temperature overnight. The reaction mixture was diluted with $CH_2Cl_2$ and washed with $H_2O$. The organic layer was concentrated under reduced pressure. The title compound was purified by HPLC using a Luna C-18 column with the following gradient: $CH_3CN/H_2O$=20/80 to 100/00 (v/v) in 45 min. The title compound was then lyophilized from a mixture of 1,4-dioxane and $H_2O$.

Yield: 76 mg
MS-ESI: $[M+H]^+$=498.2
HPCL: $R_t$=13.90 min, column 5 µm Luna C-18(2) 150*4.60 mm, flow 1 ml/min, detection 210 nm, eluent $H_2O/CH_3CN$=40/60 to 0/100 (v/v) in 15 min

Example 9 tert-Butyl 5-amino-2-methylthio-4-(3-(p-toluenesulfonamido)-phenyl)-thieno[2,3-d]pyrimidine-6-carboxamide (a). 5-Cyano-4-(3-nitrophenyl)-2-methylthio-6-hydroxy-pyrimidine A mixture of S-methylisothiourea sulfate (69.0 g), 3-nitrobenzaldehyde (75.0 g), ethyl cyanoacetate (56.0 ml) and potassium carbonate (72.5 g) in abs. EtOH (1500 ml) was stirred at 60° C. for 16 h. The reaction mixture was cooled to 0° C. in an ice bath. The resulting precipitate was filtered off, washed with abs. EtOH and dissolved in hot water (100° C.). The solution was cooled to room temperature, acidified with 2N HCl to pH 2 and cooled to 0° C. in an ice bath. The resulting precipitate was filtered off and washed with ice water. Residual water in the precipitate was removed by coevaporation with 1,4-dioxane.

Yield: 54.0 mg.
MS-ESI: $[M+H]^+$=289.0
TLC: $R_f$=0.3, silica gel, DCM/MeOH=9/1 (v/v).

(b). 6-Chloro-5-cyano-4-(3-nitrophenyl)-2-methylthio-pyrimidine $POCl_3$ (100 ml) was added to a stirred solution of 5-cyano-4-(3-nitrophenyl)-2-methylthio-6-hydroxy-pyrimidine (example 9(a), 25.0 g) in dry 1,4-dioxane (300 ml). After 3 h at 90° C., the mixture was cooled to room temperature and concentrated under reduced pressure. The residue was dissolved in 1,4-dioxane (100 ml) and the resulting solution was cooled to 0° C. Ice water was cautiously added. The resulting precipitate was filtered off and washed with water. Residual water in the precipitate was removed by coevaporation with 1,4-dioxane.

Yield: 26.0 g.

MS-ESI: [M+H]$^+$=307.0

TLC: $R_f$=0.5, silica gel, heptane/EtOAc=3/2 (v/v).

(c). Ethyl 5-cyano-4-(3-nitrophenyl)-2-methylthio-6-(ethoxycarbonylmethylthio)-pyrimidine DIPEA (15.7 ml) was added to a stirred solution of ethyl 2-mercaptoacetate (9.3 ml) and 6-chloro-5-cyano-4-(3-nitrophenyl)-2-methylthio-pyrimidine (example 9(b), 26.0 g) in a mixture of EtOH (250 ml) and DCM (250 ml). After 1 h at room temperature, 0.1N aq. HCl (500 ml) was added to the mixture which was then extracted with DCM (3*500 ml), dried (MgSO$_4$) and concentrated under reduced pressure.

Yield: 28.0 g

MS-ESI: [M+H]$^+$=390.4

TLC: $R_f$=0.5, silica gel, heptane/EtOAc=3/2 (v/v).

(d). Ethyl 5-amino-4-(3-nitrophenyl)-2-methylthio-thieno[2,3-d]pyrimidine-6-carboxylate A mixture of ethyl 5-cyano-4-(3-nitrophenyl)-2-methylthio-6-(ethoxycarbonylmethylthio)-pyrimidine (example 9(c), 28.0 g) and DIPEA (30 ml) in a mixture of toluene (150 ml) and EtOH (150 ml) was stirred at reflux temperature (100° C.) for 16 h. The mixture was then cooled to room temperature and concentrated under reduced pressure. Residual DIPEA was removed by coevaporation with toluene.

Yield: 28.0 g

MS-ESI: [M+H]$^+$=391.2

TLC: $R_f$=0.6, silica gel, heptane/EtOAc=3/2 (v/v).

(e). tert-Butyl 5-amino-2-methylthio-4-(3-aminophenyl)-thieno[2,3-d]-pyrimidine-6-carboxamide Ethyl 5-amino-2-methylthio-4-(3-nitrophenyl)-thieno[2,3-d]-pyrimidine-6-carboxylate (example 9d, 780 mg) was dissolved in 1,4-dioxane (10 ml). Ethanol (10 ml) and tin(II) chloride (1.1 g) were added and the reaction mixture was stirred overnight at 90° C. After concentration of the reaction mixture in vacuo, the residue was redissolved in EtOAc (50 ml) and washed with 4M aq. NaOH (10 ml), dried (MgSO$_4$) and concentrated under reduced pressure. The ethyl ester group in the resulting derivative ethyl 5-amino-2-methylthio-4-(3-aminophenyl)-thieno[2,3-d]-pyrimidine-6-carboxylate (558 mg) was saponified to the corresponding acid (430 mg) using the method described in example 1d and subsequently reacted with tert-butylamine (200 µl) to form the corresponding tert-butylamide (according to example 1e). The title compound was purified by chromatography on silicagel with hept/EtOAc=3/1 (v/v) as eluent.

Yield: 391 mg

MS-ESI: [M+H]$^+$=388.0

TLC: $R_f$=0.43, silica gel, hept/EtOAc=3/2 (v/v)

(f). tert-Butyl 5-amino-2-methylthio-4-(3-(p-toluenesulfonamido)-phenyl)-thieno[2,3-d]pyrimidine-6-carboxamide tert-Butyl 5-amino-2-methylthio-4-(3-aminophenyl)-thieno[2,3-d]pyrimidine-6-carboxamide (example 9e, 100 mg) was dissolved in dry pyridine (5 ml). p-Toluenesulfonyl chloride (70 mg) was added and the mixture was stirred at room temperature for 2 h. The reaction mixture was diluted with CH$_2$Cl$_2$ and washed with 0.1M aq. HCl. The organic layer was dried (MgSO$_4$) and concentrated under reduced pressure. The title compound was purified by chromatography on silica gel with hept/EtOAc=3/2 (v/v) as eluent.

Yield: 63 mg

MS-ESI: [M+H]$^+$=542.4

HPCL: $R_t$=23.46 min, column Luna C-18 (see example 1e), eluent phosphate buffer 50 mM pH 2.1/H$_2$O/CH$_3$CN/CH$_3$OH=10/72/17/1 to 10/18/68/4 (v/v) in 50 min Example 10 tert-Butyl 5-amino-2-methylthio-4-(3-(vinylsulfonamido)-phenyl)-thieno[2,3-d]pyrimidine-6-carboxamide tert-Butyl 5-amino-2-methylthio-4-(3-aminophenyl)-thieno[2,3-d]pyrimidine-6-carboxamide (example 9e, 2.5 g) was dissolved in a mixture of CH$_2$Cl$_2$ (25 ml) and pyridine (25 ml). 2-Bromo-ethanesulfonyl chloride was prepared as described in *Bull. Chem. Soc. Jpn.* 39, 1937-1941 (1966). A solution of 2-bromo-ethanesulfonyl chloride (2 g) in CH$_2$Cl$_2$ (5 ml) was added dropwise and the mixture was stirred at room temperature for 2 h. The reaction mixture was diluted with CH$_2$Cl$_2$ and washed with sat. aq. NaHCO$_3$. The organic layer was dried (MgSO$_4$) and concentrated under reduced pressure. The title compound was purified by chromatography on silica gel with hept/EtOAc=3/2 (v/v) as eluent.

Yield: 1.4 g

MS-ESI: [M+H]$^+$=478.6

TLC: $R_f$=0.80, silica gel, hept/EtOAc=3/2 (v/v)

Example 11 tert-Butyl 5-amino-2-methylthio-4-(3-(2-piperidino-ethanesulfonamido)-phenyl)-thieno[2,3-d]pyrimidine-6-carboxamide tert-Butyl 5-amino-2-methylthio-4-(3-(vinylsulfonamido)-phenyl)-thieno[2,3-d]pyrimidine-6-carboxamide (example 10, 87 mg) was dissolved in dry THF (5 ml). Piperidine (181 µl) was added and the reaction mixture was stirred at room temperature overnight. The reaction mixture was diluted with CH$_2$Cl$_2$ and washed with sat. aq. NaHCO$_3$. The organic layer was dried (MgSO$_4$) and concentrated under reduced pressure. The title compound was first purified by chromatography on silica gel with hept/EtOAc=3/2 (v/v) as eluent and then by HPLC using a Luna C-18 column with the following gradient: CH$_3$CN/0.1% aq. trifluoroacetic acid (TFA)=10/90 to 90/10 (v/v) in 30 min. The title compound was then lyophilized from a mixture of 1,4-dioxane and 0.1% aq TFA.

Yield: 89 mg (TFA salt)

MS-ESI: [M+H]$^+$=563.4

HPCL: $R_t$=18.4 min, column Luna C-18 (see example 1e), eluent H$_2$O/CH$_3$CN=60/40 to 0/100 (v/v) in 25 min

Example 12 tert-Butyl 5-amino-2-methylthio-4-(3-(2-(thiomorpholin-4-yl)-ethanesulfonamido)-phenyl)-thieno[2,3-d]pyrimidine-6-carboxamide Reaction of thiomorpholine (184 µl) with tert-butyl 5-amino-2-methylthio-4-(3-(vinylsulfonamido)-phenyl)-thieno[2,3-d]pyrimidine-6-carboxamide (example 10, 87 mg) was performed according to the method described in example 11. The title compound was first purified by chromatography on silica gel with hept/EtOAc=3/2 (v/v) as eluent and then by HPLC using a Luna C-18 column with the following gradient: $CH_3CN/0.1\%$ aq. TFA=10/90 to 90/10 (v/v) in 30 min. The title compound was then lyophilized from a mixture of 1,4-dioxane and 0.1% aq TFA.

Yield: 120 mg (TFA salt)

MS-ESI: $[M+H]^+$=581.2

HPCL: $R_t$=17.2 min, column Luna C-18 (see example 1e), eluent $H_2O/CH_3CN$=60/40 to 0/100 (v/v) in 25 min

Example 13 tert-Butyl 5-amino-2-methylthio-4-(3-(2-(bis-(2-methoxyethyl)-amino)-ethanesulfonamido)-phenyl)-thieno[2,3-d]pyrimidine-6-carboxamide Reaction of bis-(2-methoxyethyl)amine (244 mg) with tert-butyl 5-amino-2-methylthio-4-(3-(vinylsulfonamido)-phenyl)-thieno[2,3-d]pyrimidine-6-carboxamide (example 10, 87 mg) was performed according to the method described in example 11. The title compound was first purified by chromatography on silica gel with hept/EtOAc=3/2 (v/v) as eluent and then by HPLC using a Luna C-18 column with the following gradient: $CH_3CN/0.1\%$ aq. TFA=10/90 to 90/10 (v/v) in 30 min. The title compound was then lyophilized from a mixture of 1,4-dioxane and 0.1% aq TFA.

Yield: 60 mg (TFA salt)

MS-ESI: $[M+H]^+$=611.4

HPCL: $R_t$=17.9 min, column Luna C-18 (see example 1e), eluent $H_2O/CH_3CN$=60/40 to 0/100 (v/v) in 25 min

Example 14 tert-Butyl 5-amino-2-methylthio-4-(3-(2-(N-methylpiperazino)-ethanesulfonamido)-phenyl)-thieno[2,3-d]pyrimidine-6-carboxamide Reaction of N-methyl piperazine (184 µl) with tert-butyl 5-amino-2-methylthio-4-(3-(vinylsulfonamido)-phenyl)-thieno[2,3-d]pyrimidine-6-carboxamide (example 10, 87 mg) was performed according to the method described in example 11. The title compound was first purified by chromatography on silica gel with hept/EtOAc=3/2 (v/v) as eluent and then by HPLC using a Luna C-18 column with the following gradient: $CH_3CN/0.1\%$ aq. TFA=10/90 to 90/10 (v/v) in 30 min. The title compound was then lyophilized from a mixture of 1,4-dioxane and 0.1% aq TFA.

Yield: 85 mg (TFA salt)

MS-ESI: $[M+H]^+$=578.4

HPCL: $R_t$=16.1 min, column Luna C-18 (see example 1e), eluent $H_2O/CH_3CN$=60/40 to 0/100 (v/v) in 25 min

Example 15 tert-Butyl 5-amino-2-methylthio-4-(3-(methoxycarbonylamino)-phenyl)-thieno[2,3-d]pyrimidine-6-carboxamide tert-Butyl 5-amino-2-methylthio-4-(3-aminophenyl)-thieno[2,3-d]pyrimidine-6-carboxamide (example 9e, 100 mg) was dissolved in dry $CH_2Cl_2$ (5 ml). Methyl chloroformate (199 µl) and DIPEA (500 µl) were added and the reaction mixture was stirred at room temperature overnight. The reaction mixture was washed with $H_2O$. The organic layer was dried ($MgSO_4$) and concentrated under reduced pressure. The title compound was purified by HPLC using a Luna C-18 column with the following gradient: $CH_3CN/10\%$ aq. $CH_3CN$=10/90 to 90/10 (v/v) in 30 min. The title compound was then lyophilized from a mixture of 1,4-dioxane and $H_2O$.

Yield: 80 mg

MS-ESI: $[M+H]^+$=446.2

HPCL: $R_t$=20.44 min, column Luna C-18 (see example 1e), eluent phosphate buffer 50 mM pH 2.1/$H_2O$/$CH_3CN$=10/72/18 to 10/18/72 (v/v) in 20 min

Example 16 tert-Butyl 5-amino-2-methylthio-4-(3-(allyloxycarbonylamino)-phenyl)-thieno[2,3-d]pyrimidine-6-carboxamide The reaction of tert-butyl 5-amino-2-methylthio-4-(3-aminophenyl)-thieno[2,3-d]pyrimidine-6-carboxamide (example 9e, 100 mg) with allyl chloroformate (274 µl) was performed using the methods described in example 15. The title compound was purified by HPLC using a Luna C-18 column with the following gradient: $CH_3CN/10\%$ aq. $CH_3CN$=10/90 to 90/10 (v/v) in 30 min. The title compound was then lyophilized from a mixture of 1,4-dioxane and $H_2O$.

Yield: 66 mg

MS-ESI: $[M+H]^+$=472.2

HPCL: $R_t$=22.37 min, column Luna C-18 (see example 1e), eluent phosphate buffer 50 mM pH 2.1/$H_2O$/$CH_3CN$=10/72/18 to 10/18/72 (v/v) in 20 min

Example 17 tert-Butyl 5-amino-2-methylthio-4-(3-(benzyloxycarbonylamino)-phenyl)-thieno[2,3-d]pyrimidine-6-carboxamide The reaction of tert-butyl 5-amino-2-methylthio-4-(3-aminophenyl)-thieno[2,3-d]pyrimidine-6-carboxamide (example 9e, 100 mg) with benzyl chloroformate (368 µl) was performed using the methods described in example 15. The title compound was purified by HPLC using a Luna C-18 column with the following gradient: $CH_3CN/10\%$ aq. $CH_3CN$=10/90 to 90/10 (v/v) in 30 min. The title compound was then lyophilized from a mixture of 1,4-dioxane and $H_2O$.

Yield: 112 mg

MS-ESI: $[M+H]^+$=522.4

HPCL: $R_t$=24.10 min, column Luna C-18 (see example 1e), eluent phosphate buffer 50 mM pH 2.1/$H_2O$/$CH_3CN$=10/72/18 to 10/18/72 (v/v) in 20 min

Example 18 tert-Butyl 5-amino-2-methylthio-4-(3-(ethoxycarbonylamino)-phenyl)-thieno[2,3-d]pyrimidine-6-carboxamide The reaction of tert-butyl 5-amino-2-methylthio-4-(3-aminophenyl)-thieno[2,3-d]pyrimidine-6-carboxamide (example 9e, 100 mg) with ethyl chloroformate (247 µl) was performed using the methods described in example 15. The title compound was purified by HPLC using a Luna C-18 column with the following gradient: $CH_3CN/10\%$ aq. $CH_3CN=10/90$ to 90/10 (v/v) in 30 min. The title compound was then lyophilized from a mixture of 1,4-dioxane and $H_2O$.
Yield: 74 mg
MS-ESI: $[M+H]^+=460.4$
HPCL: $R_t=21.77$ min, column Luna C-18 (see example 1e), eluent phosphate buffer 50 mM pH 2.1/$H_2O$/$CH_3CN=10/72/18$ to 10/18/72 (v/v) in 20 min

Example 19 tert-Butyl 5-amino-2-methylthio-4-(3-(phenoxycarbonylamino)-phenyl)-thieno[2,3-d]pyrimidine-6-carboxamide The reaction of tert-butyl 5-amino-2-methylthio-4-(3-aminophenyl)-thieno[2,3-d]pyrimidine-6-carboxamide (example 9e, 100 mg) with phenyl chloroformate (324 µl) was performed using the methods described in example 15. The title compound was purified by HPLC using a Luna C-18 column with the following gradient: $CH_3CN/10\%$ aq. $CH_3CN=10/90$ to 90/10 (v/v) in 30 min. The title compound was then lyophilized from a mixture of 1,4-dioxane and $H_2O$.
Yield: 47 mg
MS-ESI: $[M+H]^+=508.4$
HPCL: $R_t=23.25$ min, column Luna C-18 (see example 1e), eluent phosphate buffer 50 mM pH 2.1/$H_2O$/$CH_3CN=10/72/18$ to 10/18/72 (v/v) in 20 min

Example 20 tert-Butyl 5-amino-2-methylthio-4-(3-(p-nitro-phenoxycarbonylamino]-phenyl)-thieno-[2,3-d]pyrimidine-6-carboxamide tert-Butyl 5-amino-2-methylthio-4-(3-aminophenyl)-thieno[2,3-d]pyrimidine-6-carboxamide (example 9e, 1 g) was dissolved in dry $CH_2Cl_2$ (10 ml). Subsequently, a solution of p-nitro-phenyl chloroformate (520 mg) in dry $CH_2Cl_2$ (10 ml) was added dropwise and the reaction mixture was stirred at room temperature. After 1 h, the reaction mixture was washed with $H_2O$. The organic layer was dried ($MgSO_4$) and concentrated under reduced pressure.
Yield: 1.42 g
MS-ESI: $[M+H]^+=553.6$
TLC: $R_f=0.7$, silica gel, hep/EtOAc=3/2 (v/v)

Example 21 tert-Butyl 5-amino-2-methylthio-4-(3-((morpholin-4-yl)-carbonylamino)-phenyl)-thieno[2,3-d]pyrimidine-6-carboxamide tert-Butyl 5-amino-2-methylthio-4-(3-(p-nitro-phenoxycarbonylamino)-phenyl)-thieno[2,3-d]pyrimidine-6-carboxamide (example 20, 142 mg) was dissolved in dry $CH_2Cl_2$ (5 ml). Morpholine (112 µl) and DIPEA (225 µl) were added and the reaction mixture was stirred at room temperature overnight. The reaction mixture was diluted with $CH_2Cl_2$ and washed with $H_2O$. The organic layer was concentrated under reduced pressure. The title compound was purified by HPLC using a Luna C-18 column with the following gradient: $H_2O$/$CH_3CN=80/20$ to 0/100 (v/v) in 45 min. The title compound was then lyophilized from a mixture of 1,4-dioxane and $H_2O$.
Yield: 22 mg
MS-ESI: $[M+H]^+=501.2$
HPCL: $R_t=8.62$ min, column Luna C-18 (see example 8), eluent $H_2O$/$CH_3CN=40/60$ to 0/100 (v/v) in 15 min

Example 22 tert-Butyl 5-amino-2-methylthio-4-(3-(o-anisidinocarbonylamino)-phenyl)-thieno[2,3-d]pyrimidine-6-carboxamide The urea coupling of tert-Butyl 5-amino-2-methylthio-4-(3-(p-nitro-phenoxycarbonylamino)-phenyl)-thieno[2,3-d]pyrimidine-6-carboxamide (example 20, 142 mg) with ortho-anisidine (159 mg) was performed according to the methods described in example 21. The title compound was purified by HPLC using a Luna C-18 column with the following gradient: $H_2O$/$CH_3CN=80/20$ to 0/100 (v/v) in 45 min. The title compound was then lyophilized from a mixture of 1,4-dioxane and $H_2O$.
Yield: 18 mg
MS-ESI: $[M+H]^+=537.2$
HPCL: $R_t=12.94$ min, column Luna C-18 (see example 8), eluent $H_2O$/$CH_3CN=40/60$ to 0/100 (v/v) in 15 min

Example 23 tert-Butyl 5-amino-2-methylthio-4-(3-(1,2,3,6-tetrahydropyridinocarboniylamino)-phenyl)-thieno[2,3-d]pyrimidine-6-carboxamide The urea coupling of tert-Butyl 5-amino-2-methylthio-4-(3-(p-nitro-phenoxycarbonylamino)-phenyl)-thieno[2,3-d]pyrimidine-6-carboxamide (example 20, 142 mg) with 1,2,3,6-tetrahydropyridine (118 µl) was performed according to the methods described in example 21. The title compound was purified by HPLC using a Luna C-18 column with the following gradient: $H_2O$/$CH_3CN=80/20$ to 0/100 (v/v) in 45 min. The title compound was then lyophilized from a mixture of 1,4-dioxane and $H_2O$.
Yield: 18 mg
MS-ESI: $[M+H]^+=497.2$
HPCL: $R_t=11.19$ min, column Luna C-18 (see example 8), eluent $H_2O$/$CH_3CN=40/60$ to 0/100 (v/v) in 15 min

Example 24 tert-Butyl 5-hydroxy-2-methylthio-4-(3-methoxyphenyl)-quinazoline-6-carboxamide (a). Ethyl 2-methylthio-4-(3-methoxyphenyl)-6-methyl-1,4-dihydropyrimidine-5-carboxylate A mixture of S-methylisothiourea sulfate (13.9 g), 3-methoxybenzaldehyde (7.5 g), ethyl acetoacetate (6.5 g) and sodium hydrogenocarbonate (21 g) in DMF (200 ml) was stirred at 70° C. for 18 h. The reaction mixture was cooled to room temperature, diluted with diethylether and washed with H₂O and sat. aq. NaCl. The title compound was purified by chromatography on silica gel with hept/EtOAc=3/2 (v/v) as eluent.

Yield: 7.3 g
MS-ESI: $[M+H]^+=321.0$
TLC: $R_f=0.2$, silica gel, hept/EtOAc=3/1 (v/v)

(b). Ethyl 2-methylthio-4-(3-methoxyphenyl)-6-methylpyrimidine-5-carboxylate Ethyl-2-methylthio-4-(3-methoxyphenyl)-6-methyl-1,4-dihydro-pyrimidine-5-carboxylate (example 24a, 7.65 g) was dissolved in a mixture of toluene (200 ml) and CH₂Cl₂ (100 ml). 2,3-Dichloro-5,6-dicyano-1,4-benzoquinone (5.45 g) was added and the reaction mixture was stirred at room temperature for 15 min. 0.2M aq. NaOH (250 ml) was added. The organic layer was separated, washed with H₂O (2*250 ml) and sat. aq. NaCl (2*250 ml), dried (MgSO₄) and concentrated under reduced pressure. The title compound was purified by chromatography on silica gel with hept/EtOAc=4/1 (v/v) as eluent.

Yield: 4.0 g
MS-ESI: $[M+H]^+=319.2$
TLC: $R_f=0.4$, silica gel, hept/EtOAc=3/1 (v/v)

(c). Ethyl 5-hydroxy-2-methylthio-4-(3-methoxyphenyl)-quinazoline-6-carboxylate A solution of ethyl 2-methylthio-4-(3-methoxyphenyl)-6-methylpyrimidine-5-carboxylate (example 24b, 318 mg) in dry THF (2 ml) was added to a freshly prepared solution of LDA in dry THF (1 ml) cooled to −78° C. The mixture was stirred at −78° C. for 30 min and 3-ethoxy acrylate (217 μl) was added. The mixture was then stirred for 3 h at −78° C. up to room temperature. 0.1M aq. HCl (20 ml) was added to the reaction mixture which was subsequently extracted with EtOAc (25 ml). The organic layer was washed with water (25 ml) and sat. aq. NaCl (25 ml), dried (MgSO₄) and concentrated under reduced pressure. The title compound was purified by chromatography on silica gel with hept/EtOAc=3/1 (v/v) as eluent and recrystallized from CH₃OH.

Yield: 38 mg
MS-ESI: $[M+H]^+=371.2$
TLC: $R_f=0.6$, silica gel, hept/EtOAc=2/3 (v/v)

(d). tert-Butyl 5-hydroxy-2-methylthio-4-(3-methoxyphenyl)-quinazoline-6-carboxamide Ethyl-5-hydroxy-2-methylthio-4-(3-methoxyphenyl)-quinazoline-6-carboxylate (example 24c, 38 mg) was dissolved in a mixture of 1,4-dioxane (4 ml) and 1M aq. KOH (0.5 ml). The mixture was refluxed for 48 h, then cooled down to room temperature and acidified by adding 0.1M aq. HCl (15 ml). The mixture was extracted with CH₂Cl₂ (15 ml). The organic layer was dried (MgSO₄) and evaporated under reduced pressure to give 5-hydroxy-4-(3-methoxyphenyl)-2-methylthio-quinazoline-6-carboxylic acid. The latter was dissolved in DMF (2 ml). tert-Butylamine (53 μl) and TBTU (96 mg) were added and the mixture was stirred at room temperature for 3 h. EtOAc (15 ml) was added and the organic layer was washed with sat. aq. NaHCO₃ (15 ml) and sat. aq. NaCl (15 ml), dried (MgSO₄) and evaporated under reduced pressure. The title compound was first purified by chromatography on silica gel with hept/EtOAc=7/3 (v/v) as eluent. It was then purified by HPLC with the following gradient: 10% aq. CH₃CN/CH₃CN/0.1% aq. TFA=57/40/3 to 7/90/3 (v/v) in 30 min. The title compound was lyophilized from a mixture of water and 1,4-dioxane.

Yield: 25 mg
MS-ESI: $[M+H]^+=398.2$
HPCL: $R_t=9.75$ min, column Luna C-18 (see example 1e), eluent phosphate buffer 50 mM pH 2.1/H₂O/CH₃CN/CH₃OH=5/35/57/3 to 5/10/81/4 (v/v) in 15 min

Example 25 tert-Butyl 5-amino-2-methylthio-4-(3-methoxyphenyl)-quinazoline-6-carboxamide

(a). 5-Cyano-4-(3-methoxyphenyl)-2-methylthio-6-vinyl-pyrimidine

6-Chloro-5-cyano-4-(3-methoxyphenyl)-2-methylthio-pyrimidine (example 1b, 1.46 g) was suspended in 1,4-dioxane (10 ml). Tetrakis(triphenylphosphine)palladium(0) (350 mg) was added and the mixture was flushed with a nitrogen atmosphere. Tetravinyltin (1.26 ml) was added and the mixture was refluxed for 5 h. The reaction mixture was then poured in a mixture of EtOAc (100 ml) and H₂O (100 ml). The organic layer was washed with sat. aq. NaCl, dried (MgSO₄) and concentrated under reduced pressure. The title compound was purified by chromatography on silica gel with hept/CH₂Cl₂=1/0 to 1/3 (v/v).

Yield: 1.05 g
MS-ESI: $[M+H]^+=284.2$
TLC: $R_f=0.4$, silica gel, hept/CH₂Cl₂=1/2 (v/v)

(b). 5-Cyano-4-(3-methoxyphenyl)-2-methylthio-6-(1,1-bis-(ethoxycarbonyl)prop-3-yl)pyrimidine 5-Cyano-4-(3-methoxyphenyl)-2-methylthio-6-vinyl-pyrimidine (example 25a) was dissolved in a mixture of ethanol (2 ml) and toluene (2 ml). Potassium carbonate (690 mg) and diethylmalonate (272 μl) were added and the mixture was stirred at room temperature for 4 h. The reaction mixture was then poured in a mixture of 0.5M aq. HCl (25 ml) and EtOAc (50 ml). The organic layer was washed with H₂O (50 ml) and sat. aq. NaCl (50 ml), dried (MgSO₄) and concentrated under reduced pressure. The title compound was purified by chromatography on silica gel with toluene/EtOAC=100/0 to 95/5 (v/v) as eluent.

Yield: 344 mg
MS-ESI: $[M+H]^+=444.2$
TLC: $R_f=0.3$, silica gel, toluene/EtOAc=95/5 (v/v)

(c). Ethyl 5-amino-2-methylthio-4-(3-methoxyphenyl)-7,8-dihydroquinazoline-6-carboxylate 5-Cyano-4-(3-methoxyphenyl)-2-methylthio-6-(1,1-bis (ethoxycarbonyl)prop-3-yl)pyrimidine (example 25b, 81 mg) was dissolved in dry CH₂Cl₂ (1 ml). A 1M solution of tin(IV) chloride in CH₂Cl₂ (1 ml) was added dropwise and the mixture was stirred at room temperature for 1 h. H₂O (10 ml) and EtOAc (10 ml) were then added to the reaction mixture. The organic layer was washed with H₂O (10 ml) and sat. aq. NaCl (10 ml), dried (MgSO₄) and concentrated under reduced pressure. The title compound was purified by chromatography on silica gel with hept/EtOAc=1/0 to 3/2 (v/v) as eluent.

Yield: 24 mg
MS-ESI: $[M+H]^+=372.2$
TLC: $R_f=0.5$, silica gel, hept/EtOAc=3/1 (v/v)

(d). Ethyl 5-amino-2-methylthio-4-(3-methoxyphenyl)-quinazoline-6-carboxylate Ethyl 5-amino-2-methylthio-4-(3-methoxyphenyl)-7,8-dihydroquinazoline-6-carboxylate (example 25c, 22 mg) was dissolved in $CH_2Cl_2$ (1 ml). A 0.06M solution of 2,3-dichloro-5,6-dicyano-1,4-benzoquinone in $CH_2Cl_2$ (1.2 ml) was added and the mixture was stirred at room temperature for 15 min. The reaction mixture was concentrated under reduced pressure. The title compound was purified by chromatography on silica gel with toluene/EtOAc=95/5 (v/v) as eluent.

Yield: 20 mg
MS-ESI: $[M+H]^+=370.0$
TLC: $R_f=0.3$, silica gel, hept/EtOAc=1/3 (v/v)

(e). 5-Amino-2-methylthio-4-(3-methoxyphenyl)-quinazoline-6-carboxylic acid

Ethyl 5-amino-2-methylthio-4-(3-methoxyphenyl)-quinazoline-6-carboxylate (example 25d, 490 mg) was dissolved in 15 ml 1,4-dioxane and a 2 M aqueous KOH solution (3 ml) was added. The mixture was heated at reflux for 5 h and at 70° C. for 76 h. The mixture was cooled to room temperature and a 0.5 M HCl-solution in water was added. The mixture was extracted with $CH_2Cl_2$ (2×50 ml), the combined organic layers were dried ($MgSO_4$) and concentrated under reduced pressure to yield the crude title compound.

Yield: 406 mg (crude)
MS-ESI: $[M+H]^+=342.2$
TLC: $R_f=0.0$, silica gel, hept/EtOAc=2/3 (v/v)

(f). tert-Butyl 5-amino-2-methylthio-4-(3-methoxyphenyl)-quinazoline-6-carboxamide To a 1.8 M solution of 5-amino-2-methylthio-4-(3-methoxyphenyl)-quinazoline-6-carboxylic acid in DMF (1.8 ml) were added TBTU (173 mg) and tert-butylamine (95 µl). The reaction mixture was stirred for 2 h and then poured into a mixture of EtOAc (25 ml) and saturated aqueous $NaHCO_3$ (50 ml). The organic phase was separated and washed with 0.5 M aqueous HCl (50 ml) and brine (50 ml), followed by drying ($MgSO_4$) and concentration under reduced pressure. The title compound was purified by chromatography on silica gel using hept/EtOAc=1/0 to 2/3 (v/v) as the eluent. The title compound was lyophilized from a mixture of dioxane and water containing 1.5 equiv. of HCl.

Yield: 44 mg
MS-ESI: $[M+H]^+=397.2$
HPLC: $R_t=21.52$ min, column Luna C-18 (see example 1e), eluent phosphate buffer 50 mM pH 2.1/$H_2O$/$CH_3CN$=10/70/20 to 10/10/80 (v/v) in 20 min

Example 26 tert-Butyl 5-amino-2-methylthio-4-(3-(2-(pyrrolidin-1-yl)-ethoxy)-phenyl)-quinazoline-6-carboxamide

(a). tert-Butyl 5-amino-2-methylthio-4-(3-hydroxyphenyl)-quinazoline-6-carboxamide A solution of tert-butyl 5-amino-2-methylthio-4-(3-methoxyphenyl)-quinazoline-6-carboxamide (example 25f, 1.5 g) in dry $CH_2Cl_2$ was cooled to 0° C. A solution of $BBr_3$ (1.1 ml) in $CH_2Cl_2$ (25 ml) was added dropwise and after the addition was complete, the mixture was stirred for 3 h at room temperature. The mixture was diluted with $CH_2Cl_2$ and a saturated aqueous $NaHCO_3$ solution (200 ml) was carefully added. The mixture was vigorously stirred for 1.5 h until all solids dissolved. The aqueous layer was extracted twice with $CH_2Cl_2$. The first organic layer was washed with sat. aq. $NaHCO_3$ and brine. The combined organic layers were dried ($MgSO_4$) and concentrated under reduced pressure. The title compound was purified by chromatography on silica gel with hept/EtOAc=1/0 to 1/1 (v/v) as eluent.

Yield: 930 mg
MS-ESI: $[M+H]^+=383.4$
TLC: $R_f=0.3$, silica gel, hept/EtOAc=2/3 (v/v)

(b). tert-Butyl 5-amino-2-methylthio-4-(3-(2-(pyrrolidin-1-yl)-ethoxy)-phenyl)-quinazoline-6-carboxamide A mixture of $K_2CO_3$ (1.0 g), 1-(2-chloroethyl)pyrrolidine hydrochloride (66 mg) and tert-butyl 5-amino-2-methylthio-4-(3-hydroxyphenyl)-quinazoline-6-carboxamide (example 26a, 121 mg) in acetone was heated overnight at reflux. The mixture was cooled to room temperature, the solids were removed by filtration and the filtrate concentrated under reduced pressure. The residue was taken up in EtOAc and washed with water and brine. The organic phase was dried ($MgSO_4$) and concentrated in vacuo. The title compound was purified by HPLC using a Luna C-18 column with the following gradient: 10% aq. $CH_3CN$/$CH_3CN$/0.1% aq. TFA=72/25/3 to 27/70/3 (v/v/v) in 30 min. The title compound was lyophilized from a mixture of water, TFA and $CH_3CN$.

Yield: 42 mg (TFA salt)
MS-ESI: $[M+H]^+=480.4$
HPLC: $R_t=12.93$ min, column Luna C-18 (see example 1e), eluent phosphate buffer 50 mM pH 2.1/$H_2O$/$CH_3CN$=10/70/20 to 10/10/80 (v/v) in 20 min

Example 27 tert-Butyl 5-amino-2-methylthio-4-(3-aminophenyl)-quinazoline-6-carboxamide

(a). 5-Cyano-2-methylthio-4-(3-nitro-phenyl)-6-[(triphenylphosphanylidene)-methyl]-pyrimidine To a suspension of anhydrous methyltriphenylphosphonium bromide (29.5 g) in dimethoxyethane (400 ml) at −78° C. was added a 1.6 M solution of n-butyllithium in hexanes. The mixture was stirred at −78° C. for 1 h and a solution of 6-chloro-5-cyano-4-(3-nitrophenyl)-2-methylthio-pyrimidine (example 9b, 10.1 g,) in dimethoxyethane (100 ml) was added and the cooling bath removed. After 1 h the reaction was complete and water (15 ml) was added. Removal of the solids by filtration was followed by concentration of the reaction mixture gave a dark residue which was stirred with ethylacetate to give a suspension. Filtration, washing of the residue with water and brine and drying of the organic layer with $MgSO_4$ was followed by concentration in vacuo. The title compound was purified by chromatography on silica gel with hept/EtOAc=4/1 to 1/1 (v/v) as eluent.

Yield: 7.04 g
MS-ESI: $[M+H]^+=299.2$
TLC: $R_f=0.4$, silica gel, hept/EtOAc=3/2 (v/v)

(b). 5-Cyano-2-methylthio-4-(3-nitro-phenyl)-6-vinyl-pyrimidine

A solution of 5-cyano-2-methylthio-4-(3-nitro-phenyl)-6-[(triphenylphosphanylidene)-methyl]-pyrimidine (example 27a, 7.04 g,)) in THF (64 ml) was treated with aqueous formaldehyde (37 wt. %, 3.55 ml) at 60° C. for 1 h. After the mixture was cooled to room temperature, it was diluted with EtOAc (100 ml) and washed with water (2×50 ml), dried (MgSO$_4$) and concentrated under reduced pressure. The title compound was purified by chromatography on silica gel using hept/EtOAc=9/1 to 3/2 (v/v) as the eluent.

Yield: 1.42 g
MS-ESI: [M+H]$^+$=547.2
TLC: R$_f$=0.6, silica gel, hept/EtOAc=3/2 (v/v)

(c). tert-butyl ethyl (2-(5-cyano-2-methylthio-4-(3-nitro-phenyl)-pyrimidin-6-yl)-ethyl)-malonate Potassium carbonate (1.88 g) and tert-butyl ethylmalonate were suspended in EtOH (82 ml) and a solution of 5-cyano-2-methylthio-4-(3-nitro-phenyl)-6-vinylpyrimidine (example 27b, 2.71 g) in toluene/CH$_2$Cl$_2$ (33 ml) was slowly added (ca 1.5 h). After the addition was complete, the mixture was stirred for an additional 40 min. The mixture was diluted with EtOAc and washed with water (2×) and brine. The organic layer was dried (MgSO$_4$) and concentrated under reduced pressure. The title compound was purified by chromatography on silica gel with hept/CH$_2$Cl$_2$=1/1 (v/v) as eluent.

Yield: 1.42 g
MS-ESI: [M+H]$^+$=487.2
TLC: R$_f$=0.5, silica gel, hept/EtOAc=3/2 (v/v)

(d). Ethyl 5-amino-2-methylthio-4-(3-nitro-phenyl)-7,8-dihydro-quinazoline-6-carboxylate A solution of tert-butyl ethyl {2-[5-cyano-2-methylthio-4-(3-nitro-phenyl)-pyrimidin-6-yl]-ethyl}-malonate (example 27c, 1.40 g) in CH$_2$Cl$_2$ (15 ml) was cooled to 0° C. A solution of SnCl$_4$ (1 M in CH$_2$Cl$_2$, 11.5 ml) was added dropwise, the ice-bath removed and the solution was stirred for an additional 30 min at room temperature. Water (64 ml) and EtOAc (64 ml) were added and the mixture was vigorously stirred until al solids dissolved. The organic phase was washed with water and brine, dried (MgSO$_4$) and concentrated under reduced pressure, giving the title compound as a crude product.

Yield: 1.19 g (crude)
MS-ESI: [M+H]$^+$=387.2
TLC: R$_f$=0.5, silica gel, hept/EtOAc=3/2 (v/v)

(e). Ethyl 5-amino-2-methylthio-4-(3-nitro-phenyl)-quinazoline-6-carboxylate A solution of crude ethyl 5-amino-2-methylthio-4-(3-nitro-phenyl)-7,8-dihydro-quinazoline-6-carboxylate (example 27d, 1.19 g) in CH$_2$Cl$_2$ (31 ml) was cooled to 0° C. A solution of DDQ (1.14 g) in toluene (31 ml) was added dropwise, the ice-bath removed and the solution was stirred for an additional 30 min at room temperature. The mixture was diluted with CH$_2$Cl$_2$ (ca 100 ml) and washed with a saturated aqueous solution of NaHCO$_3$ (3×100 ml) and brine (2×50 ml). The combined aqueous layers were back-extracted with CH$_2$Cl$_2$. The combined organic layers were dried (MgSO$_4$) and concentrated under reduced pressure. The title compound was purified by chromatography on silica gel using hept/EtOAc=9/1 to 3/2 (v/v) as eluent.

Yield: 735 mg
MS-ESI: [M+H]$^+$=385.2
TLC: R$_f$=0.5, silica gel, hept/EtOAc=3/2 (v/v)

(f). Ethyl 5-amino-2-methylthio-4-(3-aminophenyl)-quinazoline-6-carboxylate

To a mixture of ethyl 5-amino-2-methylthio-4-(3-nitrophenyl)-quinazoline-6-carboxylate (example 27e, 1.54 g) and SnCl$_2$.2H$_2$O (4.52 g) in 1,4-dioxane (35 ml) were added EtOH (35 ml) and concentrated aqueous HCl (690 µl). The reaction mixture was stirred at 90° C. for 5 h. After cooling to room temperature and concentration under reduced pressure the residue was suspended in EtOAc (35 ml). The mixture was brought to pH 10 by the addition of 2 M NaOH and THF and brine were added. The resulting mixture was stirred for 40 min, after which time the organic layer was separated, dried (MgSO$_4$) and concentrated under reduced pressure. The title compound was purified by chromatography on silica gel using hept/EtOAc=9/1 to 3/2 (v/v) as eluent.

Yield: 818 mg
MS-ESI: [M+H]$^+$=355.2
TLC: R$_f$=0.3, silica gel, hept/EtOAc=3/2 (v/v)

(g). 5-amino-2-methylthio-4-(3-aminophenyl)-quinazoline-6-carboxylic acid

A solution of 5-amino-2-methylthio-4-(3-aminophenyl)-quinazoline-6-carboxylate (example 27f, 658 mg) in 1,4-dioxane was treated with an aqueous solution of KOH (2 M, 4.2 ml) at 70° C. for 18 h. After the reaction mixture was cooled to room temperature, it was acidified to pH 1 with 4 N HCl. The mixture was extracted with CH$_2$Cl$_2$ (3×). The combined organic layers were dried (MgSO$_4$) and concentrated under reduced pressure to give the crude title compound.

Yield: 215 mg
MS-ESI: [M+H]$^+$=327.2
TLC: R$_f$=0, silica gel, hept/EtOAc=3/2 (v/v)

(h). tert-Butyl 5-amino-2-methylthio-4-(3-aminophenyl)-quinazoline-6-carboxamide The conversion of 5-amino-2-methylthio-4-(3-aminophenyl)-quinazoline-6-carboxylic acid (example 27g, 192 mg) to the corresponding tert-butyl amide was performed according to the procedure described in example 1e. The title compound was purified by chromatography on silica gel using hept/EtOAc=9/1 to 3/2 (v/v) as eluent.

Yield: 243 mg
MS-ESI: [M+H]$^+$=382.2
HPCL: R$_t$=6.57 min, column Luna C-18 (see example 1e), eluent H$_2$O/CH$_3$CN=45/55 to 0/100 (v/v) in 20 min

Example 28 tert-Butyl 5-amino-2-methylthio-4-(3-(2-(morpholin-4-yl)-acetamido)-phenyl)-quinazoline-6-carboxamide

(a). tert-Butyl 5-amino-2-methylthio-4-(3-(2-bromoacetamido)-phenyl)-quinazoline-6-carboxamide To a suspension of tert-butyl 5-amino-2-methylthio-4-(3-aminophenyl)-quinazoline-6-carboxamide (example 27h, 791 mg) in CH$_2$Cl$_2$ (60 ml) was added DIPEA (1.08 ml), followed by the slow addition of bromoacetyl chloride (242 μl) in CH$_2$Cl$_2$ (20 ml). After 40 min at room temperature the reaction mixture was washed with sat. aqueous NHCO$_3$ (3×), followed by drying (MgSO$_4$) and concentration under reduced pressure. The crude title compound was used without further purification in the next step.

Yield: 1.20 g (crude)

MS-ESI: [M+H]$^+$=504.2

TLC: R$_f$=0.4, silica gel, hept/EtOAc=3/2 (v/v)

(b). tert-Butyl 5-amino-2-methylthio-4-(3-(2-(morpholin-4-yl)-acetamido)-phenyl)-quinazoline-6-carboxamide To a solution of tert-butyl 5-amino-2-methylthio-4-(3-(2-bromoacetamido)-phenyl)-quinazoline-6-carboxamide (example 28a, 88 mg) in acetonitrile was added morpholine (148 μl) and the mixture was stirred for 18 h. After this time CH$_2$Cl$_2$ (15 ml) was added and the mixture was washed with sat. aqueous NaHCO$_3$. The organic layer was dried (MgSO$_4$) and concentrated in vacuo. The title compound was purified by chromatography on silica gel using CH$_2$Cl$_2$/MeOH=1/0 to 9/1 (v/v) as eluent. The title compound was lyophilized from a mixture of acetonitrile and water containing 1.5 equiv. of HCl.

Yield: 82 mg (HCl salt)

MS-ESI: [M+H]$^+$=509.2

HPCL: R$_t$=13.00 min, column Luna C-18 (see example 1e), eluent H$_2$O/CH$_3$CN=75/25 to 0/100 (v/v) in 20 min Example 29 tert-Butyl 5-amino-2-methylthio-4-(3-((N-(tert-butyl)-glycinyl)-amino)-phenyl)-quinazoline-6-carboxamide Reaction of tert-butylamine (275 μl) with tert-butyl 5-amino-2-methylthio-4-(3-(2-bromoacetamido)-phenyl)-quinazoline-6-carboxamide (example 28a, 130 mg) was performed according to the method described in example 28b. The title compound was first purified by chromatography on silica gel with hept/EtOAc=3/2 (v/v) as eluent and then by HPLC using a Luna C-18 column with the following gradient: CH$_3$CN/0.1% aq. TFA=10/90 to 90/10 (v/v) in 30 min. The title compound was then lyophilized from a mixture of 1,4-dioxane and aq HCl.

Yield: 28 mg (HCl salt)

MS-ESI: [M+H]$^+$=495.4

HPCL: R$_t$=12.93 min, column Luna C-18 (see example 1e), eluent phosphate buffer 50 mM pH 2.1/H$_2$O/CH$_3$CN=10/70/20 to 10/10/80 (v/v) in 20 min.

Example 30

Ethyl 5-amino-2-methylthio-4-(3-nitrophenyl)-7-hydroxy-pyrido[2,3-d]pyrimidine-6-carboxylate (a). 6-Amino-5-cyano-2-methylthio-4-(3-nitrophenyl)pyrimidine A solution of 6-chloro-5-cyano-4-(3-nitrophenyl)-2-methylthio-pyrimidine (example 9b, 10.0 g) was treated with ammonium hydroxide (28% NH$_3$ in water, 15 ml) and the mixture was stirred overnight. The formed crystals were collected by filtration and washed with water. The product was dried at 50° C. under vacuum yielding the title compound.

Yield: 8.9 g

MS-ESI: [M+H]$^+$=288.2

TLC: R$_f$=0.3, silica gel, hept/EtOAc=3/2 (v/v)

(b). Diethyl 2-(Amino-[6-amino-2-methylthio-4-(3-nitrophenyl)-pyrimidin-5-yl]-methylene)malonate To a suspension of 6-amino-5-cyano-2-methylthio-4-(3-nitrophenyl)pyrimidine (example 30a, 5.74 g) in 1,2-dichloropropane (200 ml) was added diethylmalonate (9.1 ml). The mixture was cooled to 0° C. and a solution of SnCl$_4$ (14 ml) in 1,2-dichloropropane (50 ml) was added dropwise. After the addition was complete, the suspension was heated at reflux for 18 h. The mixture was allowed to cool to room temperature and after solids were settled the 1,2-dichloropropane was carefully decanted. The resulting solids were stirred with EtOAc (300 ml) and water (300 ml) until dissolution was complete. The organic layer was washed with water (500 ml) and brine (500 ml), dried (MgSO$_4$) and concentrated in vacuo. The title compound was purified by chromatography on silica gel using hept/EtOAc=1/0 to 3/2 (v/v) as eluent.

Yield: 3.78 g

MS-ESI: [M+H]$^+$=448.4

TLC: R$_f$=0.2, silica gel, hept/EtOAc=3/2 (v/v)

(c). Ethyl 5-amino-2-methylthio-4-(3-nitrophenyl)-7-hydroxy-pyrido[2,3-d]pyrimidine-6-carboxylate A suspension of diethyl 2-(amino-[6-amino-2-methylthio-4-(3-nitrophenyl)-pyrimidin-5-yl]-methylene)-malonate (example 30b, 1.34 g) in diphenyl ether (30 ml) was heated under a stream of nitrogen to 240° C. for 2 h. After the mixture was cooled to room temperature, heptane was added (200 ml) and the solids were collected by filtration. The title compound was purified by chromatography on silica gel using CH$_2$Cl$_2$/acetone=1/0 to 4/1 (v/v) as eluent.

Yield: 590 mg

MS-ESI: [M+H]$^+$=402.4

TLC: R$_f$=0.3, silica gel, CH$_2$Cl$_2$/acetone=9/1 (v/v)

Example 31 tert-Butyl 5-amino-2-phenyl-4-(3-((thiomorpholin-4-yl)-carbonylamino)-phenyl)-thieno[2,3-d]pyrimidine-6-carboxamide (a). 5-Cyano-4-(3-nitrophenyl)-2-phenyl-6-hydroxy-pyrimidine A mixture of benzamidine hydrochloride (16.4 g), 3-nitrobenzaldehyde (15.1 g), ethyl cyanoacetate (11.2 ml) and potassium carbonate (16.6 g) in abs. EtOH (250 ml) was stirred at 60° C. for 8 h. The reaction mixture was cooled to 0° C. in an ice bath. The resulting precipitate was filtered off, washed with abs. EtOH and heated in water (100° C.) until a clear solution was obtained. The solution was cooled to 50° C., acidified to pH 2 by adding 2N aq. HCl and cooled to 0° C. in an ice bath. The resulting precipitate was filtered off and washed with ice water. Residual water was removed by coevaporation with 1,4-dioxane.

Yield: 15.0 g.

MS-ESI: [M+H]$^+$=319.2

TLC: $R_f$=0.3, silica gel, DCM/MeOH=9/1 (v/v).

(b). 6-Chloro-5-cyano-4-(3-nitrophenyl)-2-phenyl-pyrimidine

POCl$_3$ (50 ml) was added to a stirred solution of 5-cyano-4-(3-nitrophenyl)-2-phenyl-6-hydroxy-pyrimidine (example 31(a), 15.0 g) and dimethylaniline (0.5 ml) in dry 1,4-dioxane p.a. (200 ml). After 3 h at 90° C., the warm mixture was filtered off and the filtrate was concentrated under reduced pressure. The residue was dissolved in 1,4-dioxane and ice water was added. The resulting precipitate was filtered off and washed with water. Residual water was removed by coevaporation with 1,4-dioxane.

Yield: 15.8 g

MS-ESI: [M+H]$^+$=337.4

TLC: $R_f$=0.8, silica gel, heptane/EtOAc=3/2 (v/v).

(c). Ethyl 5-cyano-4-(3-nitrophenyl)-2-phenyl-6-(ethoxycarbonylmethylthio)-pyrimidine DIPEA (8.71 ml) was added to a stirred solution of ethyl 2-mercaptoacetate (5.15 ml) and 6-chloro-5-cyano-4-(3-nitrophenyl)-2-phenyl-pyrimidine (example 31(b), 15.8 g) in a mixture of EtOH (125 ml) and DCM (125 ml) under a nitrogen atmosphere. After 2 h at room temperature, the mixture was diluted with DCM until complete dissolution, washed with 0.5N aq. HCl, dried (MgSO$_4$) and concentrated under reduced pressure.

Yield: 19.7 g

MS-ESI: [M+H]$^+$=421.2.

TLC: Rf=0.7, silica gel, heptane/EtOAc=3/2 (v/v).

(d). Ethyl 5-amino-4-(3-nitrophenyl)-2-phenyl-thieno[2,3-d]pyrimidine-6-carboxylate DIPEA (20.0 ml) was added to a stirred solution of ethyl 5-cyano-4-(3-nitrophenyl)-2-phenyl-6-(ethoxycarbonylmethylthio)-pyrimidine (example 31(c), 19.7 g) in a mixture of abs. EtOH (100 ml) and toluene p.a. (100 ml). After 48 h at 1001C, the mixture was cooled to 0° C. The resulting precipitate was filtered off, washed with cold EtOH and dried in vacuo at 40° C.

Yield: 17.0 g

MS-ESI: [M+H]$^+$=421.2

TLC: $R_f$=0.5, silica gel, heptane/EtOAc=3/2 (v/v).

(e). Ethyl 5-amino-4-(3-aminophenyl)-2-phenyl-thieno[2,3-d]pyrimidine-6-carboxylate A solution of tin (II) chloride (23.0 g) in abs. EtOH (250 ml) was added to a solution of ethyl 5-amino-4-(3-nitrophenyl)-2-phenyl-thieno[2,3-d]pyrimidine-6-carboxylate (example 31(d), 16.6 g) in 1,4-dioxane p.a. (250 ml). 37% aq. HCl (6.9 ml) was added and the mixture was heated under reflux (90° C.) for 16 h. The mixture was allowed to cool to room temperature and concentrated under reduced pressure. The residue was suspended in EtOAc (500 ml). 4N aq. NaOH was added to obtain a pH of 10-11. The mixture was diluted by adding sat. aq. NaCl. The organic layer was separated, dried (MgSO$_4$) and concentrated under reduced pressure.

Yield: 17.0 g

MS-ESI: [M+H]$^+$=421.2

TLC: $R_f$=0.5, silica gel, heptane/EtOAc=3/2 (v/v).

(f). 5-Amino-4-(3-aminophenyl)-2-phenyl-thieno[2,3-d]pyrimidine-6-carboxylic acid Potassium hydroxide (20.0 g) was added to a solution of ethyl 5-amino-4-(3-aminophenyl)-2-phenyl-thieno[2,3-d]pyrimidine-6-carboxylate (example 31(e), 17.0 g) in a mixture of 1,4-dioxane (210 ml) and water (80 ml). After 16 h at 90° C., the mixture was cooled to 0° C. The resulting precipitate was filtered off, suspended in water (300 ml) and cooled to 0° C. The mixture was acidified to pH 3 by adding 2N aq. citric acid and stirred at 0° C. up to room temperature for 2 h. The resulting precipitate was filtered off, washed with water and dried in vacuo at 40° C.

Yield: 13.3 g

MS-ESI: [M+H]$^+$=363.0

TLC: $R_f$=0.2, silica gel, DCM/MeOH=95/5 (v/v).

(g). tert-Butyl 5-amino-4-(3-aminophenyl)-2-phenyl-thieno[2,3-d]pyrimidine-6-carboxamide DIPEA (15.3 ml), tert-butylamine (9.3 ml) and TBTU (14.1 g) were added to a mixture of 5-amino-4-(3-aminophenyl)-2-phenyl-thieno[2,3-d]pyrimidine-6-carboxylic acid (example 31(f), 13.3 g) in a mixture of DCM (250 ml) and DMF (50 ml) under a nitrogen atmosphere. After 3 h at room temperature, the mixture was diluted with DCM and washed with sat. aq. NaHCO$_3$, O. 1N aq. HCl and sat. aq. NaCl. The organic layer was dried (MgSO$_4$) and concentrated under reduced pressure. The crude product was purified by chromatography on silica gel, using heptane/EtOAc=3/7 to 1/1 (v/v) as eluent.

Yield: 14.7 g

MS-ESI: [M+H]$^+$=418.4

TLC: $R_f$=0.4, silica gel, heptane/EtOAc=3/2 (v/v).

(h). tert-Butyl 5-amino-2-phenyl-4-(3-(p-nitro-phenoxycarbonylamino)-phenyl)-thieno[2,3-d]pyrimidine-6-carboxamide tert-Butyl 5-amino-2-phenyl-4-(3-aminophenyl)-thieno[2,3-d]pyrimidine-6-carboxamide (example 31(g), 2.0 g) was dissolved in dry CH$_2$Cl$_2$ (20 ml). Subsequently, a solution of p-nitro-phenyl chloroformate (520 mg) in dry CH$_2$Cl$_2$ (10 ml) was added dropwise and the reaction mixture was stirred at room temperature.

After 3 h, the reaction mixture was washed with H$_2$O. The organic layer was dried (MgSO$_4$) and concentrated under reduced pressure.

Yield: 2.9 g

MS-ESI: [M+H]$^+$=583.2

TLC: $R_f$=0.6, silica gel, heptane/EtOAc=1/1 (v/v).

(i). tert-Butyl 5-amino-2-phenyl-4-(3-((thiomorpholin-4-yl)-carbonylamino)-phenyl)-thieno[2,3-d]pyrimidine-6-carboxamide Thiomorpholine (300 μl) was added to a solution of tert-butyl 5-amino-2-phenyl-4-(3-(p-nitro-phenoxycarbonylamino)-phenyl)-thieno[2,3-d]pyrimidine-6-carboxamide (example 31(h), 150 mg) in dichloromethane (5 ml) and the reaction mixture was stirred at room temperature overnight.

Subsequently, the reaction mixture was diluted with $CH_2Cl_2$ and washed with $H_2O$. The organic layer was concentrated under reduced pressure. The title compound was purified by HPLC using a Luna C-18 column with the following gradient: $H_2O/CH_3CN$=80/20 to 0/100 (v/v) in 45 min. The title compound was then lyophilized from a mixture of 1,4-dioxane and $H_2O$.

Yield: 89 mg

MS-ESI: $[M+H]^+$=547.2

HPCL: $R_t$=11.71 min, column Luna C-18(2), 3 μm, 100× 2.0 mm, detection UV=210 nm, oven temperature=40° C., flow=0.25 m/min, eluent phosphate buffer 50 mM pH 2.1/ water/ACN=10/30/60 to 10/5/85 (v/v/v), run time=20 min.

Example 32 tert-Butyl 5-amino-2-phenyl-4-(3-((N,N-dimethylamino)-carbonylamino)-phenyl)-thieno[2,3-d]pyrimidine-6-carboxamide Dimethyl amine hydrochloride (150 mg) was added to a solution of N,N-diisopropylethylamine (DIPEA, 0.50 ml) and tert-butyl 5-amino-2-phenyl-4-(3-(p-nitro-phenoxycarbonylamino)-phenyl)-thieno[2,3-d]pyrimidine-6-carboxamide (example 31(h), 250 mg) in dichloromethane (5 ml) and the reaction mixture was stirred at room temperature overnight. Subsequently, the reaction mixture was diluted with $CH_2Cl_2$ and washed with $H_2O$. The organic layer was concentrated under reduced pressure. The title compound was purified by HPLC using a Luna C-18 column with the following gradient: $H_2O/CH_3CN$=80/20 to 0/100 (v/v) in 45 min. The title compound was then lyophilized from a mixture of 1,4-dioxane and $H_2O$.

Yield: 75 mg

MS-ESI: $[M+H]^+$=489.2

HPCL: $R_t$=19.58 min, column Luna C-18(2), 3 μm, 100× 2.0 mm, detection UV=210 nm, oven temperature=40° C., flow=0.25 ml/min, eluent phosphate buffer 50 mM pH 2.1/ water/ACN=10/60/30 to 10/5/85 (v/v/v), run time=20 min.

Example 33 tert-Butyl 5-amino-2-phenyl-4-(3-((morpholin-4-yl)-carbonylamino)-phenyl)-thieno[2,3-d]pyrimidine-6-carboxamide Morpholine (250 mg) was added to a solution of tert-butyl 5-amino-2-phenyl-4-(3-(p-nitro-phenoxycarbonylamino)-phenyl)-thieno[2,3-d]pyrimidine-6-carboxamide (example 31(h), 150 mg) in dichloromethane (5 ml) and the reaction mixture was stirred at room temperature overnight. Subsequently, the reaction mixture was diluted with $CH_2Cl_2$ and washed with $H_2O$. The organic layer was concentrated under reduced pressure. The title compound was purified by HPLC using a Luna C-18 column with the following gradient: $H_2O/CH_3CN$=80/20 to 0/100 (v/v) in 45 min. The title compound was then lyophilized from a mixture of 1,4-dioxane and $H_2O$.

Yield: 63 mg

MS-ESI: $[M+H]^+$=489.2

HPCL: $R_t$=19.39 min, column Luna C-18(2), 3 μm, 100× 2.0 mm, detection UV=210 nm, oven temperature=40° C., flow=0.25 ml/min, eluent phosphate buffer 50 mM pH 2.1/ water/ACN=10/60/30 to 10/5/85 (v/v/v), run time=20 min.

Example 34

CHO-LH and CHO—FSH in vitro bioactivity

LH agonistic activity of compounds was tested in Chinese Hamster Ovary (CHO) cells stably transfected with the human LH receptor and cotransfected with a cAMP responsive element (CRE)/promoter directing the expression of a firefly luciferase reporter gene. Binding of ligand to the Gs-coupled LH receptor will result in an increase of cAMP, which in turn will induce an increased transactivation of the luciferase reporter construct. The luciferase signal was quantified using a luminescence counter. For test compounds, $EC_{50}$ values (concentration of test compound causing half-maximal (50%) stimulation) were calculated. For that purpose the software program GraphPad PRISM, version 3.0 (GraphPad software Inc., San Diego) was used. Results indicated that $EC_{50}$ value for the compounds of examples 9, 11, 12, 13, 14, 25 and 27 was between $10^{-6}$ and $10^{-7}$ M. The compounds of examples 1, 2, 3, 4, 5, 17, 22, 26, 28, 29, 31, and 33 showed an $EC_{50}$ value between $10^{-7}$ and $10^{-8}$ M, whereas the $EC_{50}$ value of the compounds of examples 7, 15, 16, 18, 21, 23 and 32 were lower than $10^{-8}$ M.

We claim:

1. A bicyclic heteroaromatic compound according to general formula I, or a pharmaceutically acceptable salt thereof,

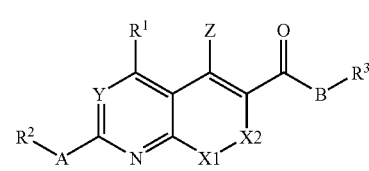

Formula I wherein
  $R^1$ is (3-8C)cycloalkyl, (2-7C)heterocycloalkyl, (6-14C)aryl or (4-13C)heteroaryl; all optionally substituted with one or more substituents selected from $N(R^4)R^5$, $NHR^5$, $R^5$, $OR^5$ and/or $SR^5$;
  $R^2$ is (1-4C)alkyl, (2-4C)alkenyl, (2-4C)alkynyl, (6-14C)aryl or (4-13C)heteroaryl;
  $R^3$ is (1-8C)alkyl, (3-8C)cycloalkyl, (2-7C)heterocycloalkyl, (6-14C)aryl or (4-13C)heteroaryl;
  $R^4$ can be selected from the same groups as described for $R^2$,
  $R^5$ is (2-7C)heterocycloalkylcarbonyl, (2-8C)alkenylsulfonyl, (2-8C)alkenoxycarbonyl, (6-14C)arylsulfonyl, (6-14C)arylaminocarbonyl, (6-14C)aryloxycarbonyl, (6-14C)arylaminosulfonyl, (6-14C)aryloxysulfonyl, or (1-8C)alkylsulfonyl, (1-8C)(di)alkylaminocarbonyl, (1-8C)alkoxycarbonyl, (1-8C)(di)alkylaminosulfonyl, or (1-8C)alkoxysulfonyl,
  the alkyl group of which may be optionally substituted with one or more substituents selected from hydroxyl, (1-8C)alkoxy, (2-7C)heterocycloalkyl(1-8C)alkoxy, (3-8C)cycloalkyl(1-8C)alkoxy, (6-14C)aryl(1-8C)alkoxy, (4-13C)heteroaryl(1-8C)alkoxy, (2-7C)heterocycloalkyl, (3-8C)cycloalkyl, (6-14C)aryl, (4-13C)heteroaryl, (1-8C)alkoxycarbonyl, (6-14C)aryloxycarbonyl, (1-8C)alkylcarbonyloxy, (6-14C)arylcarbonyloxy, (1-8C)alkylcarbonyl, (6-14C)arylcarbonyl, amine, (1-8C)alkylaminocarbonyl, (6-14C)arylaminocarbonyl, (1-8C)alkylcarbonylamino, (6-14C)arylcarbonylamino, (6-14C)(di)arylamino, (di)[(1-3C)alkoxy(1-3C)alkyl]amino and/or (1-8C)(di)alkylamino;

Y is N;

Z is NH$_2$ or OH;

A is S, N(H), N(R$^4$), O or a bond;

B is N(H) or a bond; and

X1-X2 is S or O.

2. The compound according to claim 1, wherein Z is NH$_2$.

3. The compound according to claim 1, wherein R$^1$ is (6-14C)aryl or (4-13C)heteroaryl, optionally substituted with one or more substituents selected from N(R$^4$)R$^5$, NHR$^5$, R$^5$, OR$^5$ or SR$^5$.

4. The compound according to claim 3, wherein R$^5$ is (2-7C)heterocycloalkylcarbonyl, or (1-8C)(di)alkylaminocarbonyl, the alkyl group of which may be optionally substituted with (2-7C)heterocycloalkyl, (4-13C)heteroaryl, (1-8C)alkoxycarbonyl, (1-8C)alkylaminocarbonyl, (1-8C)alkylcarbonylamino, (6-14C)arylcarbonylamino, amine and/or (1-8C)(di)alkylamino.

5. The compound according to claim 3, wherein R$^1$ is phenyl, optionally substituted with one or more substituents.

6. The compound according to claim 5, wherein R$^1$ is substituted at the meta position.

7. The compound according to claim 1, wherein B is N(H), or B is a bond and R$^3$ is (2-7C)heterocycloalkyl.

8. The compound according to claim 1, wherein X1-X2 is S.

9. A pharmaceutical composition comprising a bicyclic heteroaromatic compound according to claim 1 or a pharmaceutically acceptable salt thereof, and a pharmaceutically acceptable auxiliary.

10. A method of treating infertility in a patient in need thereof comprising:

administering to the patient an effective amount of the compound according to claim 1 or a pharmaceutically acceptable salt thereof.

* * * * *